US008802160B2

(12) United States Patent
Bentov et al.

(10) Patent No.: US 8,802,160 B2
(45) Date of Patent: *Aug. 12, 2014

(54) STABLE AMORPHOUS CALCIUM CARBONATE COMPRISING PHOSPHORYLATED AMINO ACIDS

(75) Inventors: Shmuel Bentov, M.P. Ha'ela (IL); Amir Sagi, Omer (IL); Amir Berman, Omer (IL); Assaf Shechter, Tel Aviv (IL)

(73) Assignee: Amorphical Ltd., Beer Sheva (IL)

( * ) Notice: Subject to any disclaimer, the term of this patent is extended or adjusted under 35 U.S.C. 154(b) by 533 days.

This patent is subject to a terminal disclaimer.

(21) Appl. No.: 12/739,071

(22) PCT Filed: Oct. 22, 2008

(86) PCT No.: PCT/IL2008/001362
§ 371 (c)(1),
(2), (4) Date: May 14, 2010

(87) PCT Pub. No.: WO2009/053967
PCT Pub. Date: Apr. 30, 2009

(65) Prior Publication Data
US 2010/0310677 A1      Dec. 9, 2010

(30) Foreign Application Priority Data

Oct. 22, 2007   (IL) .......................................... 186850
Aug. 14, 2008   (IL) .......................................... 193461

(51) Int. Cl.
*A61K 33/10*      (2006.01)
(52) U.S. Cl.
USPC ......................................... 424/687; 426/648
(58) Field of Classification Search
None
See application file for complete search history.

(56) References Cited

U.S. PATENT DOCUMENTS

| | | | |
|---|---|---|---|
| 4,237,147 A | 12/1980 | Merten | |
| 4,964,894 A | 10/1990 | Freepons | |
| 6,265,200 B1 | 7/2001 | De Leys | |
| 6,348,571 B1 | 2/2002 | Redei | |
| 2007/0191963 A1* | 8/2007 | Winterbottom et al. | 623/23.5 |
| 2008/0095819 A1* | 4/2008 | Gourdie et al. | 424/423 |
| 2010/0221362 A1 | 9/2010 | Bentov | |

FOREIGN PATENT DOCUMENTS

| WO | 2005115414 | 12/2005 |
|---|---|---|
| WO | 2008041236 | 4/2008 |

OTHER PUBLICATIONS

Phil. Trans. R. Soc. Lond. B 1984 304, 479-508.*
Akiva-Tal., Anat et al., (2011) In situ molecular NMR picture of bioavailable calcium stabilized as amorphous CaCO3 biomineral in crayfish gastroliths. Proc Natl Acad Sci USA 108(36):14763-14768.
Hu, Y.-Y. et al., (2010) Strongly bound citrate stabilizes the apatite nanocrystals in bone. Proc Natl Acad Sci USA 107 (52):22425-22429.
Johnsson, M. et al., (1991) Adsorption and mineralization effects of citrate and phosphocitrate on hydroxyapatite. Calcif Tissue Int 49(2):134-137.
Lee, Hyun Sook et al., (2005) Fabrication of unusually stable amorphous calcium carbonate in an ethanol medium. Materials Chemistry and Physics 93(2-3):376-382.
Loste, Eva et al., (2003) The role of magnesium in stabilising amorphous calcium carbonate and controlling calcite morphologies. Journal of Crystal Growth 254(1-2):206-218.
Ma, Zhuojun et al., (2007) A novel extrapallial fluid protein controls the morphology of nacre lamellae in the pearl oyster, *Pinctada fucata*. J Biol Chem 282(32).23253-23263.
Malkaj, P. and Dalas, E. (2007) The effect of acetaminophen on the crystal growth of calcium carbonate. J Mater Sci Mater Med 18(5):871-875.
Manoli, F. and Dalas, E. (2002) The effect of sodium alginate on the crystal growth of calcium carbonate. J Mater Sci Mater Med 13(2):155-158.
Martins, Manuel A. et al., (2008) Hydroxyapatite micro- and nanoparticles: nucleation and growth mechanisms in the presence of citrate species. J Colloid Interface Sci 318(2):210-216.
Maruyama, Koji et al., (2011) Synthesizing a composite material of amorphous calcium carbonate and aspartic acid. Materials Letters 65(2):179-181.
Reddi, A. H. et al., (1980) Influence of phosphocitrate, a potent inhibitor of hydroxyapatite crystal growth, on mineralization of cartilage and bone. Biochem Biophys Res Commun 97(1):154-159.
Rodriguez-Blanc, J. D. et al., (2012) The role of pH and Mg on the stability and crystallization of amorphous calcium carbonate. Journal of Alloys and Compounds 536(Supp 1):S477-S479 International Symposium on Metastable, Amorphous and Nanostructured Materials, ISMANAM-2011 (Jun. 26-Jul. 1, 2011).
Schneiders, Wolfgang et al., (2007) Effect of modification of hydroxyapatite/collagen composites with sodium citrate, phosphoserine, phosphoserine/RGD-peptide and calcium carbonate on bone remodelling. Bone 40 (4):1048-1059.
Sugawara, Ayae et al., (2006) Self-organization of oriented calcium carbonate/polymer composites: Effects of a matrix peptide isolated from the exoskeleton of a crayfish. Angew Chem Int Ed Engl 45(18):2676-2879 Supporting Information.
Yudkovsky, Y. (2007) Hepatopancreatic multi-transcript expression patterns in the crayfish *Cherax quadricarinatus* during the moult cycle. Insect Molecular Biology 16(6):661-674.
GenCore Database DQ847548 2012 corrsponding to Yudkovsky 2007.
U.S. Appl. No. 12/765,009 Requirement for Restriction/Election May 4, 2012.
U.S. Appl. No. 12/765,009 Non-Final Rejection Aug. 2, 2012.
Sugawara A et al: "Self-organization of oriented . . . crayfish", Angewandte Chemie-Int'l Ed. 20060428 Wiley-Vch Verlag DE, vol. 45, No. 18, Apr. 28, 2006, pp. 2876-2879, XP002517167.
Inoue Hirotaka et al: "Purification and structural . . . clarkii", Bioscience Biotech. and Biochem., vol. 65, No. 8, Aug. 2001, pp. 1840-1848, XP002517168.

(Continued)

*Primary Examiner* — Hasan Ahmed
(74) *Attorney, Agent, or Firm* — Roach Brown McCarthy & Gruber, P.C.; Kevin D. McCarthy

(57) ABSTRACT

Provided are compositions containing amorphous calcium carbonate (ACC), and at least one phosphorylated amino acid which stabilizes the amorphous form of said calcium carbonate. The compositions are useful in pharmaceutical and nutraceutical formulations.

15 Claims, 34 Drawing Sheets

(56) References Cited

OTHER PUBLICATIONS

Inoue et al: "Significance of the N- and C-... calcification", Peptides, Elsevier, Amsterdam, vol. 28, No. 3, Feb. 7, 2007, pp. 566-573, XP005877260.

Halloran B A et al: "Characterization of organic ... colbecki", Comparative Biochem. and Physiol. B, vol. 111, No. 2, 1995, pp. 221-231, XP002517169.

Saitoh E el al: "Inhibition of cacium-carbonate ... phosphoproteins", Archives of Oral Biology, Pergamon Press, GB, vol. 30, No. 8, Jan. 1, 1985, pp. 641-643, XP022866569.

Multigner L et al: "Pancreatic stone protein ... juice" Biochemical and Biophysical Research Comm, Academic Press Inc., Orlando FL, vol. 110, No. 1, Jan. 14, 1983, pp. 69-74, XP024842097.

Shechter Assaf et al: "A gastrolith protein ... matrix", Proceedings of the Nat'l Acad. of Sciences of the U.S.A., vol. 105, No. 20, May 2008, pp. 7129-7134, XP002517172.

Addadi L et al: "Taking advantage of ... biomineralization", Advanced Materials, Wiley Vch, Weinheim, DE, vol. 15, No. 12, Jun. 17, 2003, pp. 959-970, XP002460425.

Luquet G et al: "Biomineralisations in crustaceans: storage strategies", Comptes Rendus-Palevol, Elsevier, Paris FR, vol. 3, No. 6-7, Oct. 1, 2004, pp. 515-534, XP004603863.

Tsutsui Naoaki et al: :Cloning and expression ... clarkii, Zoological Science (Tokyo), vol. 16, No. 4, Aug. 1999, pp. 619-628, XP002517170.

Hecker A et al: "Phosphorylation of serine ... structures", Febs Letters, Elsevier, Amsterdam, NL, vol. 535, No. 1-3, Jan. 30, 2003, pp. 49-54, XP004404843.

Internet site http://www.uniprot.org/uniprot/P98157.html—last modified Nov. 30, 2010—22 pages—and history of when each version was released (aka, publicly disclosed)—8 pages.

PCT Written Opinion of the International Searching Authority for corresponding PCT application—Apr. 22, 2010, 14 pages.

Thomas and Birchall (1983) The retarding action of sugars on cement hydration. Cement and Concrete Research 13 (6): 830-842.

\* cited by examiner

Table 1: Comparison of amino acid compositions of GAP proteins.

| | Amino acid | GAP 12 (9.9 kDa) pI-5.09 | GAP 21 (19.5 kDa) pI-4.8 | GAP 22 (28.6 kDa) pI-11.45 | GAP 65 (60.8 kDa) pI-5.01 |
|---|---|---|---|---|---|
| Non-polar Aliphatic | Glycine | 18.4% | 9.2% (17) | 5.6% (15) | 6.1% |
| | Alanine | 15.3% | 15.7% | 8.2% (22) | 4.7% |
| | Valine | 10.2% | 7.6% (14) | 4.5% (12) | 4.5% |
| | Leucine | 4.1% (4) | 8.6% (16) | 5.9% (16) | 5.1% |
| | Isoleucine | 0% (0) | 1.6% (3) | 4.8% (13) | 4.7% |
| | Methionine | 0% (0) | 0% (0) | 0% (0) | 2.8% |
| Aromatic | Phenylalanine | 5.1% (5) | 7% (13) | 1.1% (3) | 6.4% |
| | Tyrosine | 4.1% (4) | 0.5% (1) | 0.4% (1) | 3.0% |
| | Tryptophan | 2% (2) | 0% (0) | 0% (0) | 1.9% |
| Polar Uncharged | Serine | 4.1% (4) | 6.5% (12) | 6.7% (18) | 5.3% |
| | Proline | 8.2% (8) | 8.1% (15) | 25.7% | 6.8% |
| | Threonine | 3.1% (3) | 1.6% (3) | 8.2% (22) | 5.3% |
| | Cysteine | 0% (0) | 0% (0) | 0% (0) | 4.9% |
| | Aspargine | 8.2% (8) | 5.4% (10) | 0.7% (2) | 5.9% |
| | Glutamine | 4.1% (4) | 10.8% | 4.8% (13) | 5.3% |
| Positively charged | Lysine | 2% (2) | 0% (0) | 5.6% (15) | 4.0% |
| | Histidine | 1% (1) | 0.5% (1) | 1.9% (5) | 2.1% |
| | Arginine | 3.1% (3) | 7% (13) | 9.3% (25) | 6.4% |
| Negatively charged | Aspartate | 2% (2) | 5.4% (10) | 3.3% (9) | 7.6% |
| | Glutamate | 5.1% (5) | 4.3% (8) | 3.3% (9) | 7.0% |

Fig. 12

```
AGCAGTGGTATCAACGCAGAGTACGCGGGAGTCCAGGTCCAGCTTCGTCAGGAGTTGGAC    60
ACACAATATACGGTGCTCTTGCTACTTCCACACCTGATGACGACCATAATGTTGGTGATC   120
                                        M  T  T  I  M  L  V  I     8

CTCCTTGTGGGGGCGTGTGTCGCCATACCACCCGGCCGTCCAACAGACAGCATCAGGTTC   180
 L  L  V  G  A  C  V  A  I  P  P  G  R  P  T  D  S  I  R  F    28

GTTCGGCAGACAAAACCTTTACCCCGTCCGCAACACCCACAGATCTCGCCCACACCCCCT   240
 V  R  Q  T  K  P  L  P  R  P  Q  H  P  Q  I  S  P  T  P  P    48

GCTGGCTACCAACCCAAGCCCAGGTAGATCCAACCCCGCACCCAGGTCATGTCATCCAG   300
 A  G  Y  Q  P  K  P  Q  V  D  P  T  P  H  P  G  H  V  I  Q    68

ACTCTACCAGCACATCCAAGTTCAAAACTGACCAGGCCTGCTCCACGACCCTCGCGACAC   360
 T  L  P  A  H  P  S  S  K  L  T  R  P  A  P  R  P  S  R  H    88

CAACGCAGCGCAGACGAAGTTCGACAGGGAAGTGTTCCTACCACCGCAATAGGCAAGCCC   420
 Q  R  S  A  D  E  V  R  Q  G  S  V  P  T  T  A  I  G  K  P   108

CAGACTCTGCCTCCCAAGTCCCAACTTACAAAACCAGCTGTACGGCCACAAACTCGTCCA   480
 Q  T  L  P  P  K  S  Q  L  T  K  P  A  V  R  P  Q  T  R  P   128

GCTACTCTTCCTGGGAATCTGGCTAAACCTGCTCAGCGATCCAAGAGTCTTGAAGACAGC   540
 A  T  L  P  G  N  L  A  K  P  A  Q  R  S  K  S  L  E  D  S   148

AGCTTCGCTCCTCTTCCTACTGGGCCCATTGTGGAACCAAGACCTTCCCCAGGAGAGCTG   600
 S  F  A  P  L  P  T  G  P  I  V  E  P  R  P  S  P  G  E  L   168

ACAAAACCAGCTAGTCGCCCCATTGTTGATCCCATACCTCCCGCAGGAGAACTGACAAAA   660
 T  K  P  A  S  R  P  I  V  D  P  I  P  P  A  G  E  L  T  K   188

CCAGCTAGTCGCCCCATTGTTGATCCCATACCTCCCGCAGGAGAACTGACAAAACCAGCT   720
 P  A  S  R  P  I  V  D  P  I  P  P  A  G  E  L  T  K  P  A   208

AGTCGCCCCATTGTTGATCCCATACCTCCCGCAGGAGAACTGACAAAACCAGCTAATCGT   780
 S  R  P  I  V  D  P  I  P  P  A  G  E  L  T  K  P  A  N  R   228

CCCAAGAGTGTGGATAGTGGTTTTGCTCCACTACCTACTGGACCCATTGTAGAACCCAGA   840
 P  K  S  V  D  S  G  F  A  P  L  P  T  G  P  I  V  E  P  R   248

CCACCTCCGGGAGAGCTAACAAAACCAGCTCCTCGTCCTAGGCCTCGTCCAGGGACTTA   900
 P  P  P  G  E  L  T  K  P  A  P  R  P  R  P  G  D  L   268

ACAAAACCAGCCACTCGTCCCAGGCCTCGTCCTGCGCGTCCCACACAGGCATAAAGTTTC   960
 T  K  P  A  T  R  P  R  P  R  P  A  R  P  T  Q  A  *         285

GTCTATCCCGACGTCTCATTTGCACCTGATAAGCGATAAAATC                   1003
```

Fig. 13

```
TACGCGGGGCATTTGGTCTCTGCAGCATCCGTCTTCATCATGAGGGCAGTCGTGTGTGTG    60
                                          M  R  A  V  V  C  V    7

CTTCTCGCTATTTCCGGAATGGCAAGTGCCCAGTCAGCGAGAGGCGAAACGTTTGCGCAT   120
 L  L  A  I  S  G  M  A  S  A  Q  S  A  R  G  E  T  F  A  H    27

GCCAGACCATCTGTCAACAGCTTCCAGGACTCTGCTTCCCTCTCTGCTGATCCTTCTGCT   180
 A  R  P  S  V  N  S  F  Q  D  S  A  S  L  S  A  D  P  S  A    47

GCTGCGGCTCCTCGAGCAGCCCCTGCAGCAGCCCCTGCCGCAGCTCCTGCCGCAGCTCCC   240
 A  A  A  P  R  A  A  P  A  A  A  P  A  A  A  P  A  A  A  P    67

GCACAGCAGAACTATGGGCCAAATTTCTTCGGTCCAGGACTCAACAATCCATTGGCCTTC   300
 A  Q  Q  N  Y  G  P  N  F  F  G  P  G  L  N  N  P  L  A  F    87

CCTCTCAATCCATTGGTAGCACAGCAAGCCCAGAGGATCGCTTCCTTCAACCCCAACCTC   360
 P  L  N  P  L  V  A  Q  Q  A  Q  R  I  A  S  F  N  P  N  L    107

AGAGTGTTCGTTGATATTGACGGCTCAGTTCAGCTCACTGATCAGTTCGGCCGCGAAGTT   420
 R  V  F  V  D  I  D  G  S  V  Q  L  T  D  Q  F  G  R  E  V    127

GATGAGGTCTTGGATGAGTTCGGCCGCGATGTATCTGAACTTCTCGATGTCGAAGAGCAG   480
 D  E  V  L  D  E  F  G  R  D  V  S  E  L  L  D  V  E  E  Q    147

CAAGAGGCACTTCTTCGACGTCGCCAGCAGCAACTTGACCTACAGCTGCTGCAGCAGTTC   540
 Q  E  A  L  L  R  R  R  Q  Q  Q  L  D  L  Q  L  L  Q  Q  F    167

AACAACCCTGCCTTTGGTGGTAGTGTTGGTGGACAAGCTGCTGTTGGCGGACAAACTGGT   600
 N  N  P  A  F  G  G  S  V  G  G  Q  A  A  V  G  G  Q  T  G    187

GTTGGGGGAGGATTCCCACGACAGAGATCCTTCAGAATCGTGGTGTAAGACCGCAATGAT   660
 V  G  G  G  F  P  R  Q  R  S  F  R  I  V  V  *               202

ACACCTCTTTCAAAGGTCGTAGCTACCACCTATATCACCTTTCCGTTTTTCCTGTCCCCT   720
TCTAACCTCCCTTGCTGATACTCTGGGTCACCTGACCCTGTCATCTGTTACTTTAGGTCA   780
CCTGGTCTTAATTCTTCTTATTTTCCTTCATCTGATAAGTCTTCCTAATTCTGCAACCTC   840
GTCACCTGTTCTTATCTCTATCCAGAGTATCCTAGCAGACTATCCCAGTGCTTTATCCTA   900
GCAGTGTCCCCCAACACTATTCCGTTGCTCTATTCTGAACGACCCAATTCGTTTACATAT   960
TAAACACCTGTACACGTCTTTACAATAAATTGTGAATACATTATTTGTATAAATTATTTA  1020
ATAAAGCAAGACATAAACACAAAACAAAAACAACAAAAAACAAACAACACAAAACAGTAC  1080
TCTGGCGTTGATACCACTGCTTGGCCCTATAGTGAGTCGTATTAG                 1125
```

Fig. 14

```
ACGCGGGACAGGTCAGCTATTAGAGTCGCACCAGCAACATCCTCTCCAGCAACATGAAGA   60
                                                          M  K  I    3

TTTTCATTCTCCTTGTGGTGATTGGTGTGGTGTCAGCCCAGCTTGGTGCTGGCCAGGTGG  120
 F  I  L  L  V  V  I  G  V  V  S  Q  L  G  A  G  Q  V  G     23

GAGGTGCTGCTCCAGCMCAGGGTGCTGGAGGTGCTGCTGGTGTTGGTGGTCCWGGGGCAG  180
  G  A  A  P  A  Q  G  A  G  G  A  A  G  V  G  G  P  A  A    43

CTCCTGTAAACCCCTACGGACCTAAAGTGTATGGTTCTGGCCTCAACAATCCCTTCGCCT  240
  P  V  N  P  Y  G  P  K  V  Y  G  S  G  L  N  N  P  F  A  F  63

TCCCTCACAACACGTGGGAAGTGAGTCGTGCTGCGGCGGTGGCAGCTACCAACCCCAACC  300
  P  H  N  T  W  E  V  S  R  A  A  A  V  A  A  T  N  P  N  L  83

TCTATGTGCGCGTGGAGTCTGACGGAGGCTGGGAATTCACCAACCGCTTCGGAGAGAAGG  360
  Y  V  R  V  E  S  D  G  G  W  E  F  T  N  R  F  G  E  K  V  103

TTGATGTGTACAACAGCTTCGGCCAAGAGCTTGACTAGTGCAGTCTTTATCTCCTTCTGT  420
  D  V  Y  N  S  F  G  Q  E  L  *                             113

CATTCACCTCATCTCGCCTCTATGAAGGCTGTCACCTCAATAATTTACCCCTCCCATACA  480
TCTGGATGTAAAAAAAACACAGGTTCTGTTGCTCTACAGCCCTGGCTATACAGCAGGTCT  540
GCTGCTACACAGCCCTGGCTATGCAGCAGGTCTGCTGATACACAGCCCTGGCTATACAGC  600
AGGTCTGCTGCTACACAGCCCTGGCTGTGCAGCAGGTCTGCTGATACACAGCCCTGGCTA  660
TGCAGCAGGTCTGCTGCTACACAGCCCTGGCTATGGAGCAGGTCTGCTGCTACACAGCCC  720
TGGTTATGCAGCAGTTCTGCTGTGCAAATCATTAGATACCAATTGGAGTCAGAATAAGAA  780
```

Fig. 15A

```
GAP 12   33 YGPKVYGSGLNNPFAFPHNTWEVSRAAAVAATN 65
GAP 21   55 YGPNFFGPGLNNPLAFPLNPLVAQQAQRIASFN 87
            ***:..:*.*****:*** *.   ..:*   :*: *

GAP 12   66 PNLYVRVESDGGWEFTNRFGEKVD-VYNSFGQEL  98
GAP 21   88 PNLRVFVDIDGSVQLTDQFGREVDEVLDEFGRDV  121
            *** * *: **. .::*::**.:** * :..**:::
```

STABLE AMORPHOUS CALCIUM CARBONATE COMPRISING PHOSPHORYLATED AMINO ACIDS

REFERENCE TO CO-PENDING APPLICATIONS

This application claims priority as a continuation-in-part from a 371 of international of PCT/IL2008/001362, filed on Oct. 22, 2008, which claims priority to Israeli patent application numbers (a) 186850, filed on Oct. 22, 2007 and (b) 193461 filed on Aug. 14, 2008.

FIELD OF THE INVENTION

The present invention relates to compositions comprising amorphous calcium carbonate, and to methods of preparing same, and further to compositions comprising phosphorylated amino acids or peptides. Particularly, said peptides are selected from crustacean proteins, including GAP65, GAP22, GAP21, and GAP12. Pharmaceutical and nutraceutical compositions comprising amorphous calcium carbonate and phosphorylated amino acids or peptides are provided.

BACKGROUND OF THE INVENTION

Calcium is considered to be one of the most important minerals in the human body. It is required for maintaining bone mass, is essential for exocytosis of neurotransmitters, takes part in the contraction of muscle cells, replaces sodium as the depolarizing mineral in the heart, and participates in many other physiological functions. Calcium is further an important structural element in biological systems. From protozoa to vertebrata, deposited calcium salts helps to keep rigid bodily shapes of animals, calcium phosphate being the main component of endoskeletons in the vertebrates and calcium carbonate of exoskeletons in the invertebrates. Calcium carbonate has six known polymorphs, three of which are anhydrous crystalline (i.e. calcite, aragonite and vaterite) two of which are hydrated (i.e. crystalline monohydrocalcite and ikaite) and one of which is hydrated amorphous namely amorphous calcium carbonate (ACC). The most thermodynamically stable of these forms is calcite, while the least stable is ACC. ACC is a transient polymorph that rapidly crystallizing into one of the five more stable polymorphs. Calcified exoskeletons with calcium carbonate minerals as the main constituents are widespread among echinoderms, mollusks, and arthropods, providing protection and serving as calcium storage. Some crustaceans store calcium carbonate temporarily, in an amorphous state, which makes it better available, particularly for quick mobilization during the mineralization of their new exoskeleton structures after molting. The formation of amorphous calcium carbonate in the living bodies of, for example, crayfish is rather intriguing, since amorphous minerals are usually thermodynamically unstable. Several techniques have been reported for the synthesis and stabilization of ACC, however, all known methods use either toxic materials or various organic polymers to stabilize ACC for more than three days. WO 2005/115414 employs crustacean organs for providing compositions with stable ACC which is readily available for human consumption.

In view of the general metabolic and biomechanical importance of calcium, and since ACC is a potentially more soluble and absorbable form of calcium carbonate as a dietary supplements, it is an object of the invention to provide new methods for preparing amorphous calcium carbonate.

It is another object of this invention to provide pharmaceutical and nutraceutical compositions comprising stable ACC, which exhibit higher solubility and bioavailability compared to crystalline calcium carbonate compositions.

Other objects and advantages of present invention will appear as description proceeds.

SUMMARY OF THE INVENTION

The present invention relates to a composition comprising amorphous calcium carbonate (ACC) and at least one component selected from phosphorylated amino acids and phosphorylated peptides. Said phosphorylated amino acids and phosphorylated peptides may comprise phospho-serine or phospho-threonine or both. Said phosphorylated amino acids and phosphorylated peptides stabilize the amorphous form of said calcium carbonate in the composition of the invention. In one aspect of the invention, said phosphorylated peptide originates from crustacean gastrolith. In one embodiment, the composition of the invention comprises ACC, at least one phosphorylated amino acid or peptide, and optionally at least one additional component such as chitin or chitosan.

In another aspect, the present invention relates to new crustacean peptides and their use in affecting the crystalline state of calcium carbonate and in the preparation of formulations. The invention also relates to functional fragments of said peptides. The isolated proteins related to below include GAP65, GAP22, GAP21, and GAP12 (were GAP stands for gastrolith protein); deduced amino acid sequences of said new proteins are provided herein, and they are denoted as SEQ ID NOS: 1, 9, 17 and 24. The invention provides an isolated and purified crustacean peptide having essentially a sequence selected from the group consisting of SEQ ID NO:1, SEQ ID NO:9, SEQ ID NO:17, SEQ ID NO:24, and homologues thereof. A sequence homolog according to the invention is a peptide with any insertions, deletions, and substitutions, as far as at least 90% of the sequence is preserved. The invention further includes an isolated and purified peptide comprising in its sequence a subsequence, said subsequence being a fragment of the above said crustacean GAP peptides, preferably a subsequence at least ten amino acid long. Said subsequence may have a sequence selected from, for example, SEQ ID NOS: 2 to 8, SEQ ID NOS: 10 to 16, and SEQ ID NOS: 18 to 23, or other fragments of sequences SEQ ID NO:1, SEQ ID NO:9, SEQ ID NO:17, SEQ ID NO:24. The invention provides a composition comprising one or more peptides as defined above, or their derivatives or variants or functional fragments or mixtures thereof, together with amorphous calcium carbonate (ACC). Said peptide stabilizes the amorphous form of said calcium carbonate in said composition. The term "functionally equivalent fragment, derivative, or variant" as used herein includes peptides with modifications that do not interfere with their ability to inhibit calcium carbonate crystallization.

The invention is directed to a peptide having amino acid sequence selected from SEQ ID NO:1, SEQ ID NO:9, SEQ ID NO:17, and SEQ ID NO:24, and to peptides being their sequence homologous having, preferably, at least 90% homology. A DNA sequence encoding a peptide according to the invention is a part of the invention as well. Provided in the invention is a calcium carbonate preparation containing a peptide as defined above or its derivative.

In a preferred embodiment of the invention, a calcium carbonate preparation comprising ACC is provided, said preparation being stable at least for about one month to about one year. A method of preparing stable amorphous calcium carbonate is disclosed, which comprises mixing in aqueous phase in any order a soluble salt comprising calcium, a carbonate source, and a phosphorylated amino acid or phosphorylated peptide. Said source may, for example, comprise a carbonate salt dissolved in the liquid phase, or said source may comprise gaseous carbon dioxide.

The term "stable" as used herein means not taking part readily in chemical change. Specifically, the phosphorylated amino acids of the invention, such as phospho-serine or phospho-threonine interact with calcium carbonate to inhibit its crystallization, and thus, said mixture is deemed stable as long as said inhibition persists and calcium carbonate crystallization is prevented or reduced.

In some embodiments, the amorphous calcium carbonate preparation (ACC) of the invention is stable for at least about one week to about two weeks, two weeks to about three weeks, three weeks to about one month, one month to about a month and a half, a month and a half to about two months, two months to about two months and a half, two months and a half to about thee months, three months and a half to about four months, four months to about four months and a half, four months and a half to about five months, five months to about five months and a half, five months and a half to about six months, six months to about six months and a half, six months and a half to about seven months, seven months to about seven months and a half, seven months and a half to about eight months, eight months to about eight months and a half, eight months and a half to about nine months, nine months to about nine months and a half, nine months and a half to about ten months, ten months to about ten months and a half, ten months and a half to about eleven months, or eleven months and a half to about a year.

In specific embodiments, the ACC preparation is stable in room temperature, said temperature ranging from about 10° C. to about 45° C., more specifically, 12° C. to about 30° C., more specifically, 14° C. to about 28° C., more specifically, 16° C. to about 27° C., more specifically, 18° C. to about 26° C., more specifically, 19° C., 20° C., 21° C., 22° C., 23° C., 24° C., or, most specifically, 25° C.

The invention provides a pharmaceutical formulation comprising the above said composition, containing one or more phosphorylated amino acids, or phosphorylated peptides as defined herein or their derivatives or variants or functional fragments or mixtures thereof, together with ACC. The above said composition is, in other aspect of the invention, advantageously used as a nutraceutical formulation, for example as a food additive. Said pharmaceutical formulation is preferably orally administered and may comprise fillers or solvents or additives. Thus, according to another aspect, the invention provides a dietary supplement comprising the above said composition, and further optionally other components selected from the group consisting of chitin, chitosan, and fillers. Said pharmaceutical formulation is preferably used in treating, preventing or ameliorating conditions such as bone metabolism disorders, pain, proliferative diseases, neurological disorders, immunologic disorders, cardiovascular diseases, pulmonary diseases, nutritional disorders, reproductive disorders, musculoskeletal disorders, and dental problems. Said treating may lead to disappearance of causative factors or to mitigating the symptoms. Said proliferative disease may be, for example, breast carcinoma or bronchogenic carcinoma. Said treating may comprise slowing down or inhibiting the cell proliferation in a tumor. As for said pain, it may be postoperative pain, pain after injury, pain associated with cancer, and neuropathic pain. The mentioned neurological disorder is, for example, selected from demyelinating diseases, dementias, and movement disorders. Said condition may be a degenerative disease selected from multiple sclerosis, Alzheimer's disease, and Parkinson's disease. Said condition may comprise a bone or bone marrow disorder, which may be, for example fracture or osteoporosis. According to another embodiment, the condition treated by the composition of the invention may be a neurodegenerative disorder.

Said new peptides GAP65, GAP22, GAP21, and GAP12 or their derivatives are used, in one aspect of the invention, in the manufacture of medicaments. Also provided is a method of treating a bone disorder or injury, and a method of managing pain, comprising orally administering a formulation comprising calcium carbonate and one or more of said new peptides or their derivatives. The term "derivatives" as used herein includes also peptide products obtained by alkylation, esterification, neutralization, cyclization, or oligomerization.

The invention provides a method of inhibiting the crystallization of calcium carbonate in a mixture comprising a carbonate and a calcium salt, comprising admixing into said mixture an amount of a phosphorylated amino acid or a phosphorylated peptide. Said phosphorylated amino acid or a phosphorylated peptide preferably comprises phospho-serine or phospho-threonine.

The term crystallization as used herein refers to the natural or artificial process of formation of solid crystals precipitating from a solution, melt or more rarely deposited directly from a gas. The crystallization process consists of two major events, nucleation and crystal growth. Nucleation is the step where the solute molecules dispersed in the solvent start to gather into clusters, on the nanometer scale (elevating solute concentration in a small region), that becomes stable under the current operating conditions. These stable clusters constitute the nuclei. However when the clusters are not stable, they redissolve. Therefore, the clusters need to reach a critical size in order to become stable nuclei. Such critical size is dictated by the operating conditions (temperature and supersaturation, for example). It is at the stage of nucleation that the atoms arrange in a defined and periodic manner that defines the crystal structure.

Thus, the term "inhibition of crystallization" as used herein refers to any action that interferes with the processes of crystallization as described, i.e. nucleation and crystal growth. Such interference may be, as a non limiting example, the disruption of electrostatic forces between molecules comprising the forming crystal, or prevention of a localized elevated concentration of the crystallizing molecule.

The term "inhibition" as referred to herein, relates to the retardation, retraining or reduction of a process by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

The invention provides, in one embodiment, a method of inhibiting the crystallization of calcium carbonate, comprising admixing into the crystallization or precipitation mixture an inhibitory effective amount of a peptide having a sequence selected from SEQ ID NO:1, SEQ ID NO:9, SEQ ID NO:17, and SEQ ID NO:24, or its homolog or functional fragment or derivative or variant, or of a mixture thereof. A method of inhibiting the crystallization of calcium carbonate according to the invention is provided, comprising providing a calcium salt soluble in water, and contacting said salt with a peptide selected from GAP65, GAP22, GAP21, and GAP12, or with its functionally equivalent fragment, derivative, or variant thereof, or with a mixture thereof.

In one aspect of the invention, food additives or functional foods are provided, comprising a mixture of calcium carbonate and at least one phosphorylated amino acid or peptide; said peptide, in one embodiment, having a sequence selected from the group consisting of SEQ ID NO:1, SEQ ID NO:9, SEQ ID NO:17, SEQ ID NO:24, and homologues or fragments thereof.

BRIEF DESCRIPTION OF THE DRAWINGS

The above and other characteristics and advantages of the invention will be more readily apparent through the following examples, and with reference to the appended drawings, wherein:

FIG. 1, shows the isolation of gastrolith soluble proteins, purification and partial sequencing of GAP65.

FIG. 2. comprises the complete deduced amino acid sequence of GAP65 and it bioinformatic analysis; FIG. 2A—deduced amino acid sequence of the open reading frame of GAP65, in bold is predicted signal sequence, grey boxes are possible phosphorylation sites, dark boxes at amino acids no. 72 and 173 are predicted O-glycosylation sites, light boxes are predicted N-glycosylation sites; FIG. 2B—a scheme of the GAP65 sequence showing the predicted domains: ChtBD2 is chitin binding domain 2, LDLa is low-density lipoprotein receptor domain class A, and the last one is polysaccharide deacetylase domain; FIG. 2C—3D structure of the LDLa domain based on homology to lipoprotein receptor, on the left is the NMR structure of complement-like repeat CR3 from the low density lipoprotein receptor-related protein, on the right is the predicted structure of the LDLa domain of GAP65;

FIG. 3. shows specific expression of GAP65 and its localization in the columnar epithelium of the gastrolith during induced premolt.

FIG. 5. are photos showing morphological deformities of the gastroliths following GAP65 silencing, representative gastroliths are dissected from crayfish injected with either of ecdysone and dsRNA of GAP65 (left), ecdysone and dsRNA carrier (middle), ecdysone carrier and dsRNA carrier (right);

FIG. 5A—lateral view of whole gastroliths dissected from the crayfish; FIGS. 5B and 5C—X-ray imaging of the above gastrolith prior to dissection (dorsal view);

FIG. 6. shows scanning electron microscope (SEM) micrographs of gastroliths structural deformities following GAP65 gene silencing; representative gastroliths were dissected from crayfish injected with ecdysone+GAP65 dsRNA (left) and ecdysone+dsRNA carrier (right)

FIG. 7. shows SEM images of in vitro precipitated calcium carbonate in the presence/absence of the gastrolith purified protein; FIG. 7B—a SEM image of ACC 40 days after the precipitation, demonstrating typical amorphous structures with nanospheres of 50-500 nm;

FIG. 8. shows Raman spectra of the ACC obtained by precipitation with GAP65 enriched fraction; FIG. 8B—27 days after the precipitation;

FIG. 10. shows partial sequencing of gastrolith proteins, presented are chromatograms obtained by nanospray Qtof2 following tryspin digestion, sequences of the peptides from significant peaks were obtained through MS/MS analysis.

FIG. 11. shows Raman spectra of the calcium carbonate precipitated from the solution of calcium chloride and sodium carbonate in the presence of gastrolith extract;

FIG. 12. is Table 1, showing amino acid compositions of GAP proteins;

FIG. 13. shows nucleotide sequence of GAP22 cDNA and the corresponding deduced amino acid sequence in open reading frame; the asterisks indicate stop codons and the gray highlighted sequences are the untranslated regions; the putative signal peptides in the N-terminus are underlined;

FIG. 14. shows nucleotide sequence of GAP21 cDNA and the corresponding deduced amino acid sequence in open reading frame; the symbols have the same meaning as in FIG. 13;

FIG. 15. relates to the GAP sequences; FIG. 15A shows nucleotide sequence of GAP12 cDNA and the corresponding deduced amino acid sequence in open reading frame; the symbols have the same meaning as in FIG. 13; FIG. 15B is sequence alignment of GAP12 and GAP21, amino acid positions of the two proteins are shown on the right and left, sequence identities are indicated by "h", conserved substitutions are indicated by ":", and semi-conserved substitutions are indicated by ".";

FIG. 16. to FIG. 27 show Raman Spectra described in detail in Examples 9 to 20;

FIG. 33, shows scanning electron microscope (SEM) images of three calcium carbonate preparations.

FIG. 34A: crystalline calcium carbonate (CCC); FIG. 34B: amorphous calcium carbonate (ACC); FIG. 34C: amorphous calcium carbonate with chitosan (ACC-C). The intensity is scaled differently for each spectrum, that is, the relative height of each spectrum corresponds to the strongest peak;

FIG. 35A: crystalline calcium carbonate (CCC); FIG. 35B: amorphous calcium carbonate (ACC); FIG. 35C: amorphous calcium carbonate with chitosan (ACC-C). The intensity is scaled differently for each spectrum, that is, the relative height of each spectrum corresponds to the strongest peak;

DETAILED DESCRIPTION OF THE INVENTION

It has now been found that some phosphorylated amino acids or peptides affect the precipitation of calcium carbonate in vitro, leading to the formation of amorphous form of calcium carbonate. Particularly, the effects have been observed when said peptides comprise several proteins present in the late premolt gastrolith of *Chorax quadricarinatus*. Peptides having apparent molecular weights of approximately 65 kDa, 22 kDa, 21 kDa, and 12 kDa induce precipitation of nanospheres of amorphous calcium carbonate material; in comparison, an inert protein provides $CaCO_3$ crystals. The nanoparticles show a Raman shift typical for amorphous $CaCO_3$.

Figure 11:
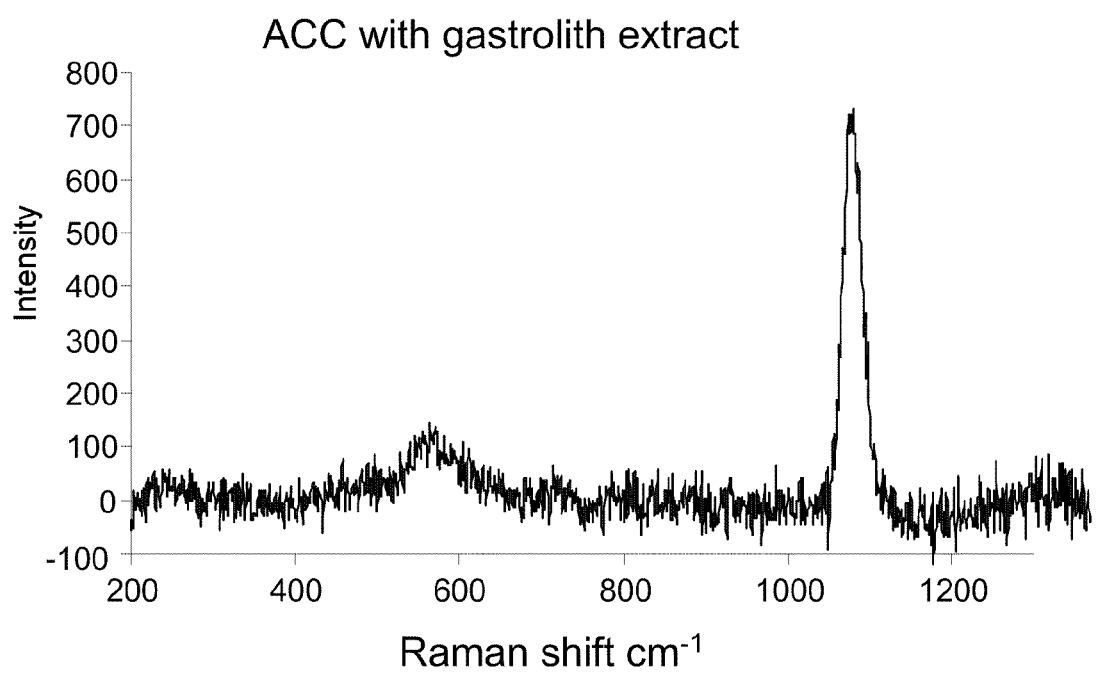

The above proteins, denoted as GAP65, GAP22, GAP21, GAP12, respectively, according to their apparent molecular weights estimated by SDS-PAGE, are involved in the precipitation and stabilization of ACC. The gastrolith extract which contains said four proteins inhibits calcium carbonate crystallization and stabilizes the amorphous form of calcium carbonate (ACC). ACC was detected by Raman spectrometry in a precipitate of $CaCO_3$ prepared from a solution containing $CaCl_2$, $Na_2CO_3$ and the gastrolith extract (FIG. 11). The presence of ACC is validated by the presence of a predominant peak at about 1080 $cm^{-1}$. Expressions of the GAP genes were found to be specific to the gastrolith epithelial disc and sub-epidermal tissue, both are cuticle related tissues. Specific expressions of the GAP peptides in several target tissues by means of RT-PCR was also studied. For example, the expression of GAP65 was found in more cuticle related tissues, whereas the expression of GAP22 was found rather in the gastrolith epithelial disc.

The cDNA sequences of the corresponding genes were obtained and their deduced proteins were found (FIGS. 2, 13-15). All four proteins were found to contain signal peptides at their N-terminus (underlined amino acids in FIGS. 13-15, bold in FIG. 2). Similarity search against databases of conserved domains revealed that GAP65 contains three conserved domains: Chitin-binding domain 2, Low density lipoprotein receptor domain class A, and Polysaccharide deacetylase domain. GAP 12, GAP 21 and GAP 22, on the other hand, show no significant similarity to any known domain. Blast, alignment of GAP 12 and GAP 21 revealed a 46.3% identity in the deduced amino acid sequences of these proteins (FIG. 15). Physico-chemical analysis of the deduced proteins revealed, that the calculated molecular weights of GAPs 12, 21 and 65 are smaller than expected, 9.9, 19.5 and 60.8 kDa respectively, while that of GAP 22 is higher than expected, 28.6 kDa (Table 1). GAP 12, GAP 21 and GAP 65 have an acidic pI, therefore they are negatively charged at the physiological pH of the gastrolith (near pH 8.5). GAP 12 and GAP 21 have a high percentage of non-polar, aliphatic amino acids (glycine, alanine and valine) and a high percentage of the polar but uncharged amino acid proline (highlighted in gray in Table 1). GAP65 has a high content of acidic amino acids. GAP22 has a basic pI, therefore it is positively charged at the physiological pH of the gastrolith. Its main characteristics are a high percentage of the polar but uncharged amino acid proline and of the positively charged arginine.

Due to special features of the new proteins, provided in this invention is also a method of inhibiting the crystallization of calcium carbonate, comprising admixing into the crystallization or precipitation mixture an amount of GAP65 or a functional fragment thereof, or a derivative, or a variant thereof. In other aspect of the invention, a method is provided of inhibiting the crystallization of calcium carbonate, comprising contacting a calcium salt soluble in water with GAP65 or a functional fragment, derivative, or variant thereof.

Figure 1A:
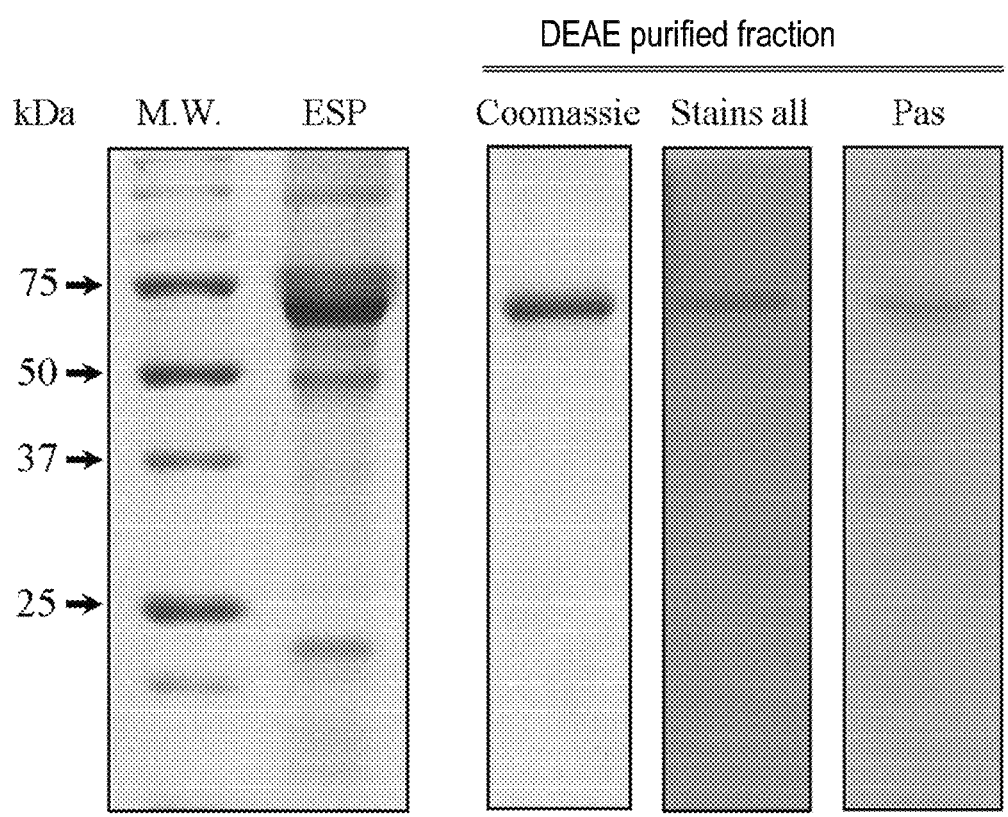
FIG. 1A—SDS-PAGE Coomassie staining of the soluble proteins profile of the gastrolith, compared to molecular weight reference proteins (left), SDS-PAGE of fraction 17 containing GAP65 purified by DEAE column chromatography stained with Coomassie, "stains all", and "pas" (right)
Figure 1B:
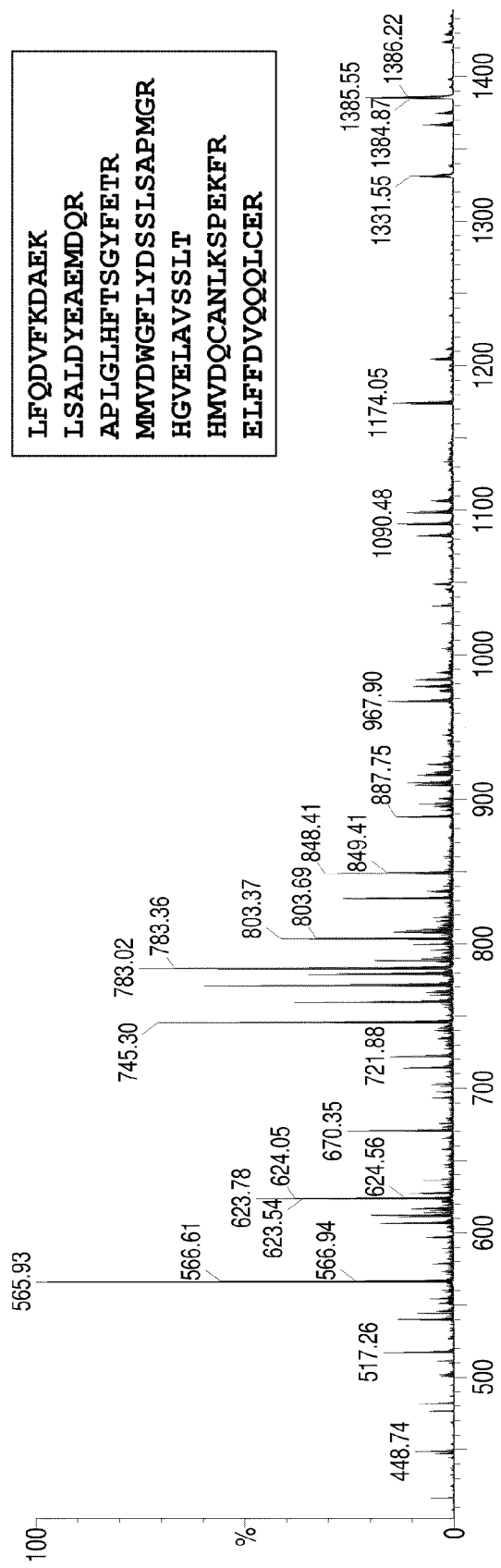
FIG. 1B—chromatogram of GAP65 obtained by nanospray Qtof2 following tryspin digestion, sequences of the peptides from significant peaks were obtained through MS/MS analysis.
Figure 2A:
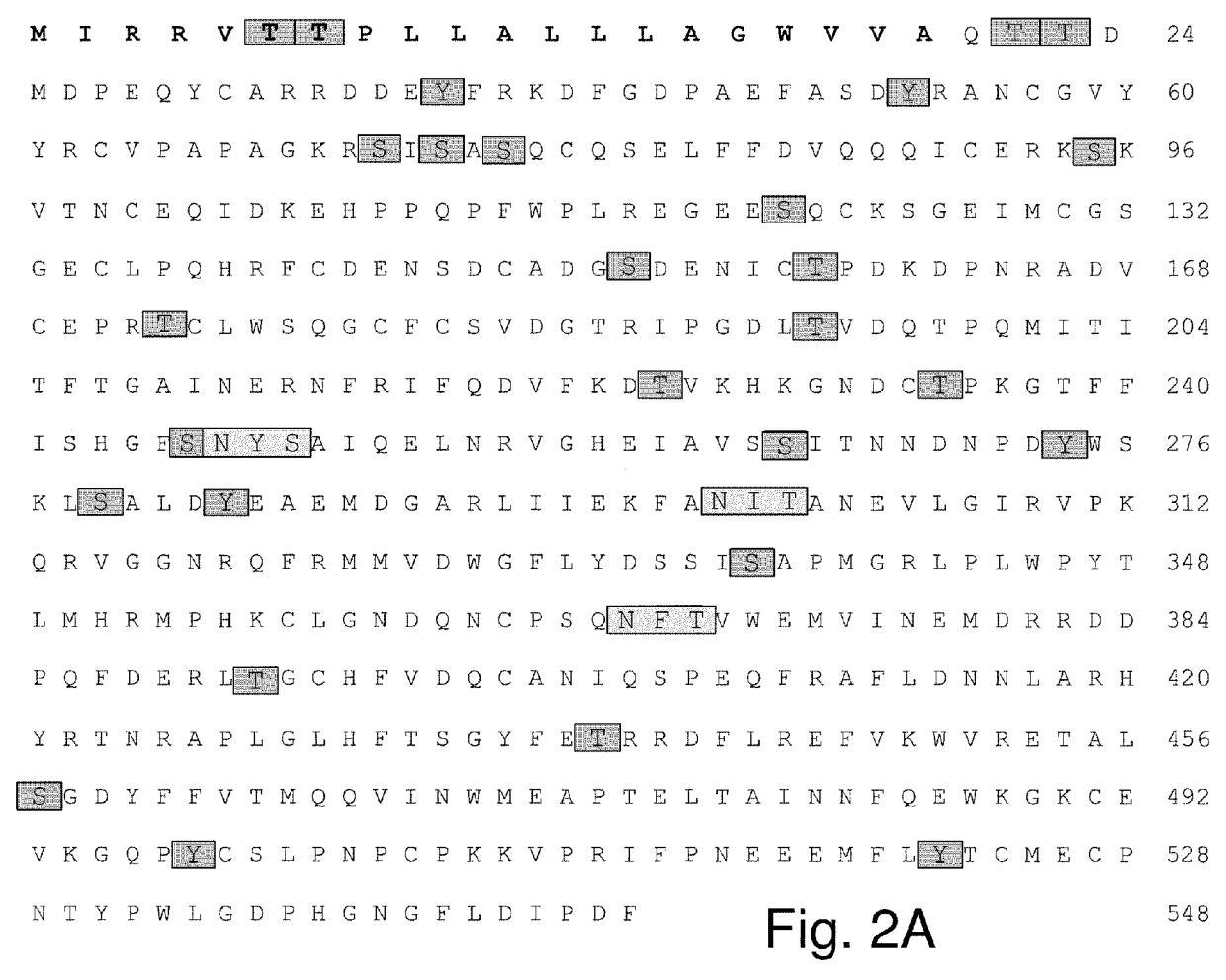
Figure 2B:
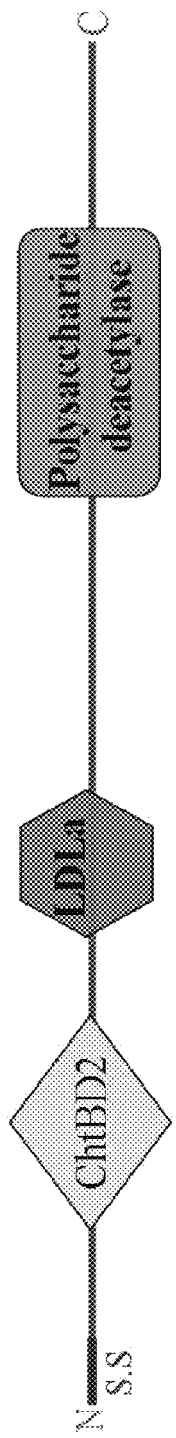
Figure 3A:
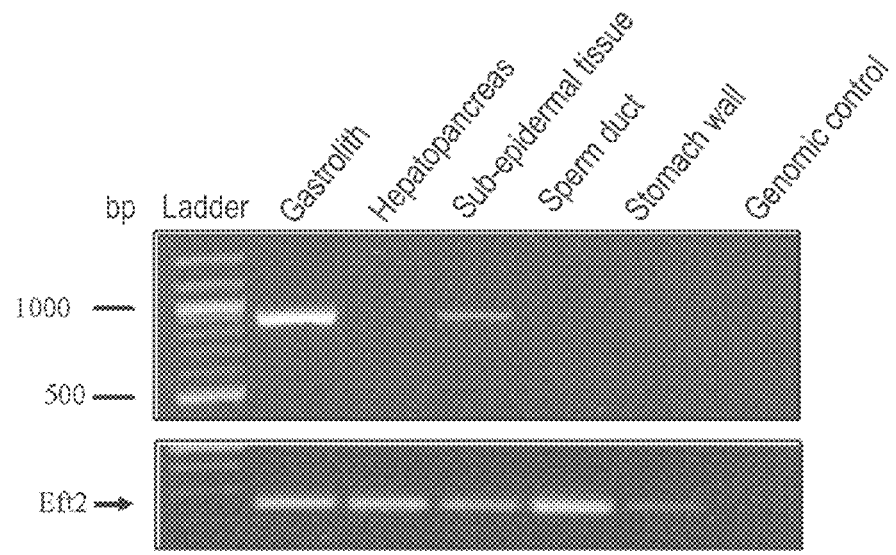
FIG. 3A—detection of GAP65 expression during premolt using RT-PCR, RNA was sampled from gastrolith epithelial disc, hepatopancreas, sub-epidermal tissue, sperm duct, and stomach wall, elongation factor 2 (Eft2) was used to reassure RNA extraction, control for genomic contamination was used.
Figure 4:
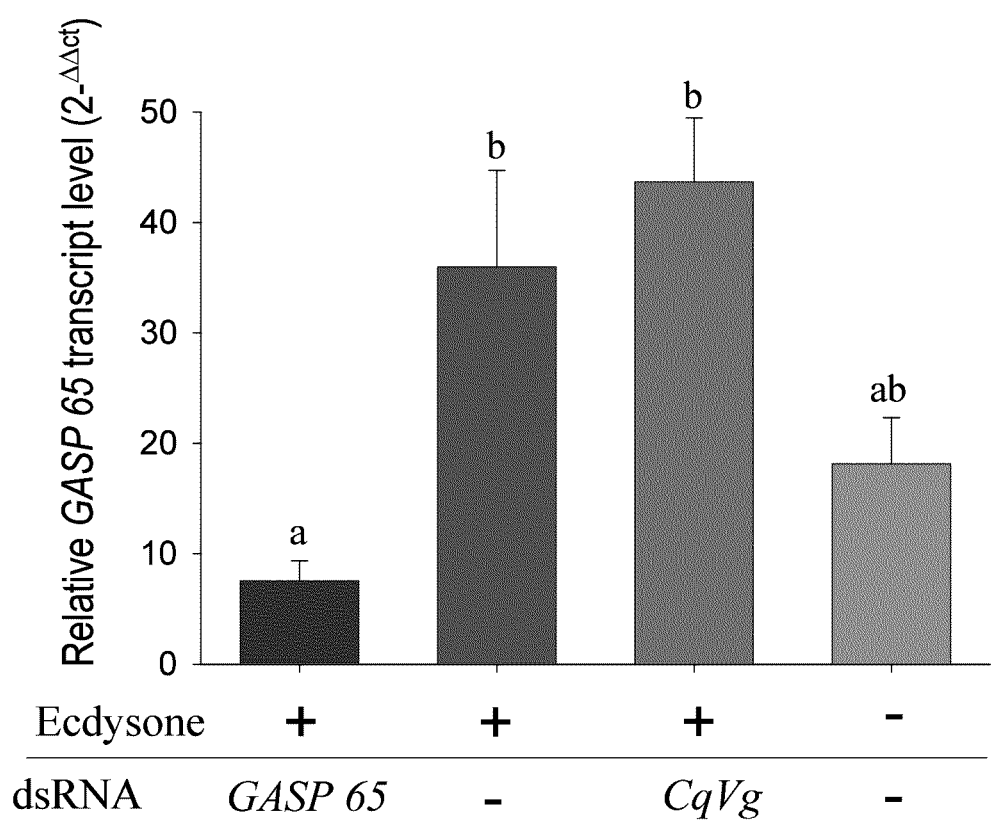
FIG. 4. shows relative transcript level of GAP65 (denoted GASP 65) in the gastrolith disc following GAP65 silencing, relative quantitation of GAP65 transcript level using real-time RT-PCR in the gastrolith disc of crayfish injected with (left to right): ecdysone and dsRNA of GAP65, ecdysone and dsRNA carrier, ecdysone and dsRNA of C. quadricarinatus vitellogenin (CqVg), ecdysone carrier and dsRNA carrier, and the letters represent statistical significance.
Figures 5A, 5B, 5C:
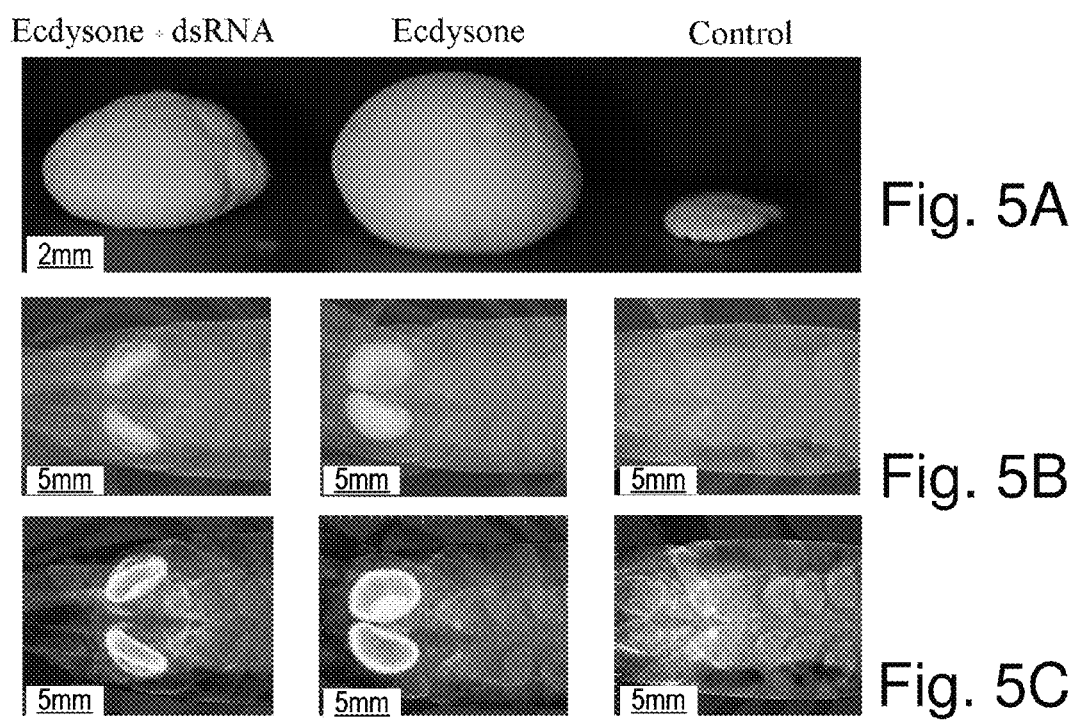

GAP65 was purified from gastrolith soluble protein extract by ion exchange chromatography, and was identified as a negatively charged glycopeptide, containing about 12 mol % Asp+Glu, based on SEQ. ID. NO. 1. Sequencing of the peptides by MS-MS provided seven oligopeptide subsequences (SEQ. ID. NO. 2-8; FIG. 1B) which were used for the construction of degenerative primers for the acquisition of a complete GAP65 encoded gene sequence based on gastrolith epithelial disc mRNA. The total deduced amino acid sequence revealed a 548 amino acids long peptide (SEQ. ID. NO. 1; FIG. 2A). Bioinformatic analysis of GAP65 sequence suggested the presence of three known domains (FIG. 2B): chitin binding domain 2 (ChtBD2) from amino acids 29-102, low-density lipoprotein receptor domain class A (LDLa), from amino acids 122-159, and polysaccharide deacetylase domain from amino acids 195-332. The LDLa domain has a predicted calcium binding property. Expression of GAP65 was tested in premolt crayfish in several target tissues by means of RT-PCR, and was detected in the gastrolith epithelial disc and in the sub-epidermal tissue, both are cuticle related tissues (FIG. 3A). In situ hybridization visualized the localization of the GAP65 expression in the gastrolith disc of induced premolt and intact intermolt crayfish (FIG. 5B). Relative GAP65 transcript levels in the gastrolith epithelial disc following silencing using GAP65 dsRNA were measured using realtime RT-PCR (FIG. 4). The role of GAP65 in gastrolith formation was tested by an RNAi technique using in vivo injections of GAP65 dsRNA to intermolt crayfish (FIG. 5). The initiation of gastrolith formation was achieved by injection of ecdysone. Morphological deformities of the gastrolith can be observed in crayfish injected with both GAP65 dsRNA and ecdysone (FIG. 5A shows dissected gastrolith, FIGS. 5B and 5C are X-ray views).

It was found that GAP65 essentially affects the micro structure of the crayfish gastrolith. Scanning electron microscope (SEM) micrographs of gastroliths dissected from crayfish injected either with GAP65 dsRNA together with ecdysone or only with ecdysone revealed severe structural abnormalities caused by the absence of GAP65 (FIG. 6). The packaging of the ACC in spherules, and the spherules size, is important for the dense packaging of the gastrolith; the absence of GAP65 led to larger spherules and less condensed structure when compared to the normal gastrolith.

In order to elucidate the role of GAP65 in the biomineralization process, an in vitro calcium carbonate precipitation was performed to test the stabilization of ACC. Electron microscope images of the precipitates distinctly indicated different polymorph composition of calcium carbonate for the precipitation in the presence/absence of GAP65-enriched fractions (FIG. 7). The precipitation of calcium carbonate in the absence of GAP, namely in the presence of an inert protein, resulted in rapid crystallization providing crystals of calcite and/or vaterite as large as 10 μm. On the other to hand, the precipitation of calcium carbonate in the presence of GAP65 resulted in amorphous $CaCO_3$ observed as a thin layer consisting of 40-60 nm spherules. The amorphous nature of the calcium carbonate in said spherules was corroborated by Raman spectra, which showed the distinct ACC peak at 1070 $cm^{-1}$, and further by employing powder x-ray diffraction (XRD), which indicated the absence of diffracting peaks from crystalline materials. The presence of GAP65 in the ACC spherules formed by the in vitro precipitation was confirmed by purification of the protein from the spherules and its identification by SDS-PAGE.

$CaCO_3$ deposits obtained by precipitation in the presence of GAP65 were initially characterized by polarized microscope, identifying calcite, vaterite, and ACC. The observations were confirmed by Raman spectroscopy and powder XRD. The ACC constituted about at least 50% of the total $CaCO_3$. The ACC remained stable under room condition for at least 1 months.

The invention, thus, provides new proteins associated with calcium metabolism in crayfish, which affect the crystalline state of calcium carbonate. Provided is a method of inhibiting the crystallization of calcium carbonate, comprising admixing into the crystallization or precipitation mixture an amount of GAP proteins or functionally equivalent fragments thereof, or derivatives, or variants thereof. The invention relates to a method of preparing ACC by admixing said new protein into a precipitation mixture, namely into a mixture in which the precipitation of $CaCO_3$ occurs, and in which precipitation of crystalline material would occur without said protein. A non-limiting example of such mixture includes an aqueous solution of calcium chloride comprising GAP65 into which a sodium carbonate solution is added. Of course the order of mixing the components may change, as well as the types of the ions sources. The concentration of GAP65 in the mixture may be, for example, about from 0.05 to 5 wt % based on the weight of $CaCO_3$. The concentration of GAP65 in the precipitation mixture may be, for example, about from 1 to 100 μg/ml.

In order to evaluate the solubility and fractional absorption of amorphous calcium carbonate stabilized by phosphorylated serine, compared to crystalline calcium carbonate, three compositions were prepared: stable calcium carbonate (ACC), stable amorphous carbonate with chitosan (ACC-C) and crystalline calcium carbonate (CCC). The presence of ACC in the compositions was confirmed by HR-SEM (FIG. 33), FTIR (FIG. 34) and Raman analysis (FIG. 35). In previous bioavailability reports in rats, calcium formulations were pre-dissolved in a carrier suspension. However, in the case of ACC, pre-dissolution would have resulted in rapid crystallization thus not applicable. In this invention, the goal was to test the bioavailability of ACC following dissolution in the stomach. For this purpose a technique that simulates oral dietary supplementation consumption and allows administration directly to the stomach using mini gelatin capsules containing 0.2% calcium was utilized.

Figure 36:
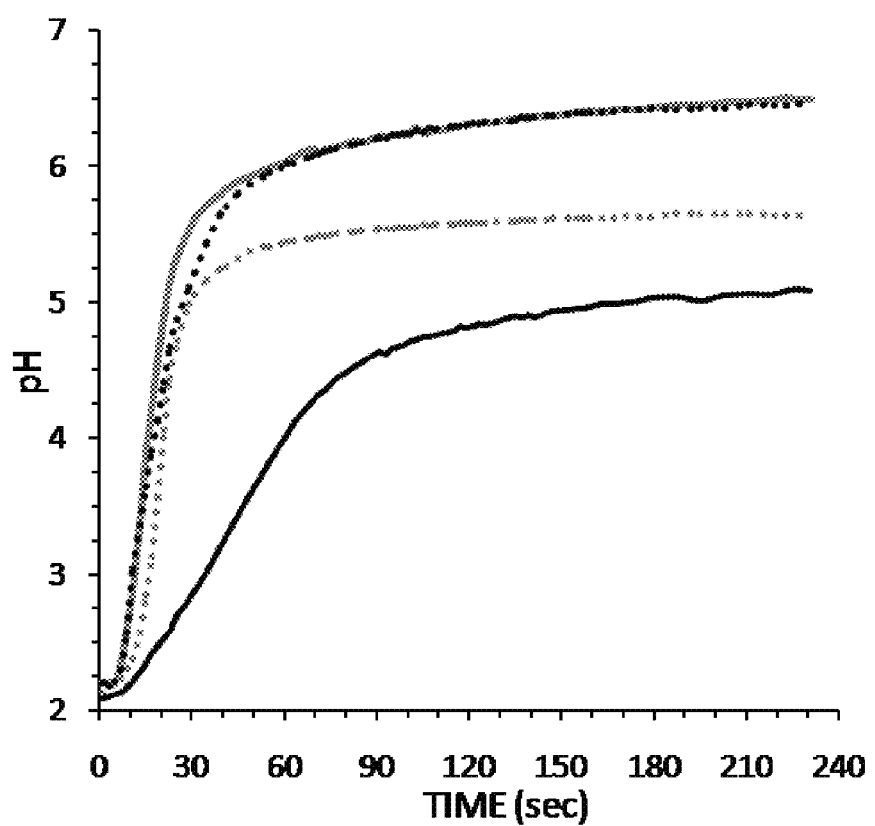
FIG. 36. shows pH changes of 0.01 M phosphoric acid following the dissolution of calcium carbonate preparations. _____ represent amorphous calcium carbonate with chitosan (ACC-C, n=5), ....... represent amorphous calcium carbonate (ACC, n=5), ....... represent crystalline calcium carbonate (CCC, n=5) and _____ represent commercial calcite (n-5)
Figure 37:
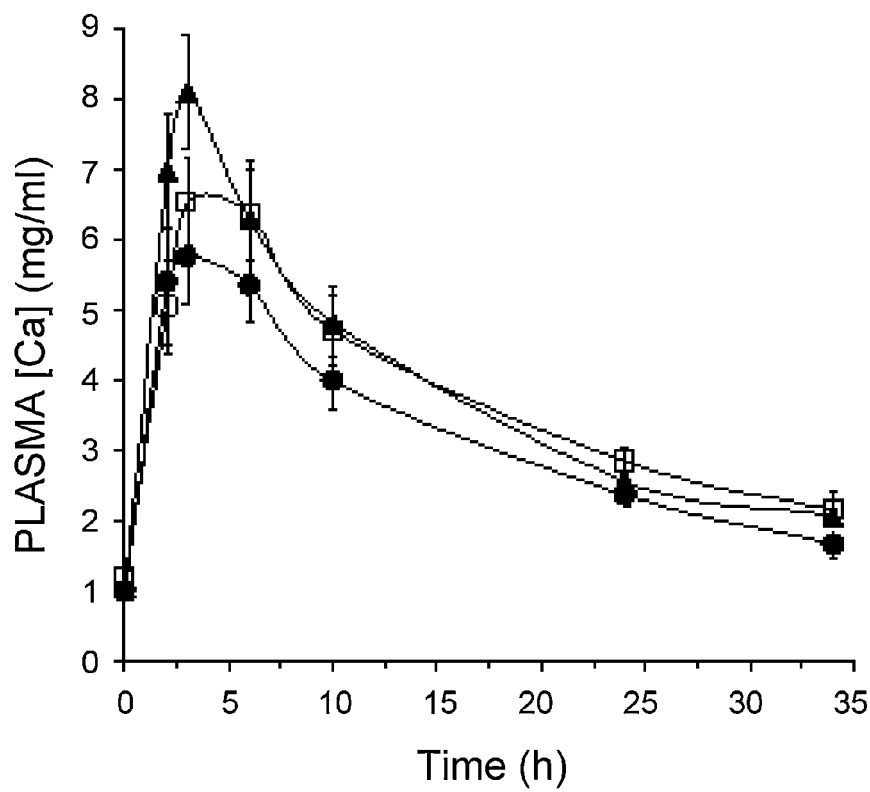
FIG. 37. shows Serum [Ca] following oral administration of calcium carbonate preparations. ●—crystalline calcium carbonate (CCC, n=13); ▲—amorphous calcium carbonate (ACC, n=13); □—amorphous calcium carbonate with chitosan (ACC-C, n=12). Bars indicate standard error of mean (SE)
Figure 38:
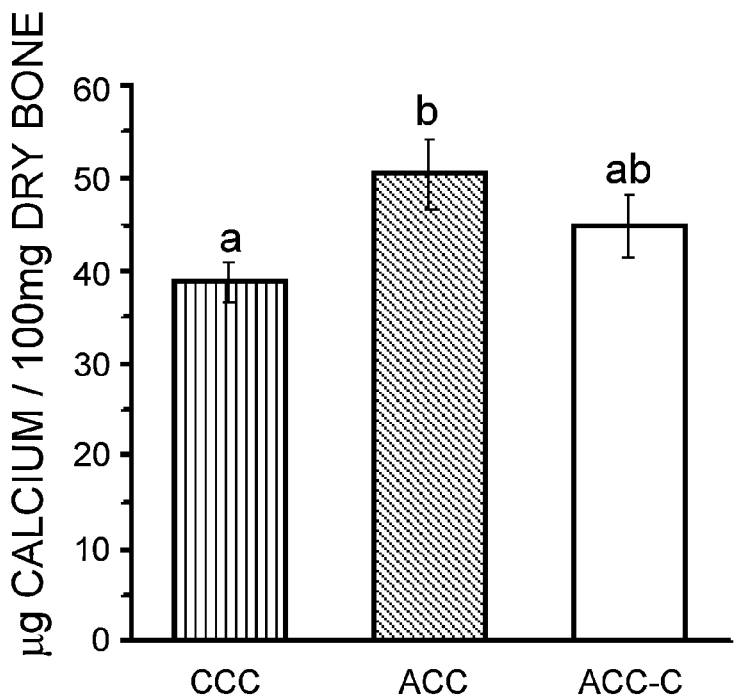
FIG. 38. shows calcium content in the femur following oral administration of radioactive calcium carbonate preparations. Content of calcium was normalized to 100 mg dry bone weight. From left to right: Crystalline calcium carbonate (CCC, n=13), amorphous calcium carbonate (ACC, n=13) and amorphous calcium carbonate with chitosan (ACC-C, n=12). Bars indicate standard error of mean (SE). Different superscript letters represent statistical significance (Statistical significance was determined by ANOVA)
Figure 39:
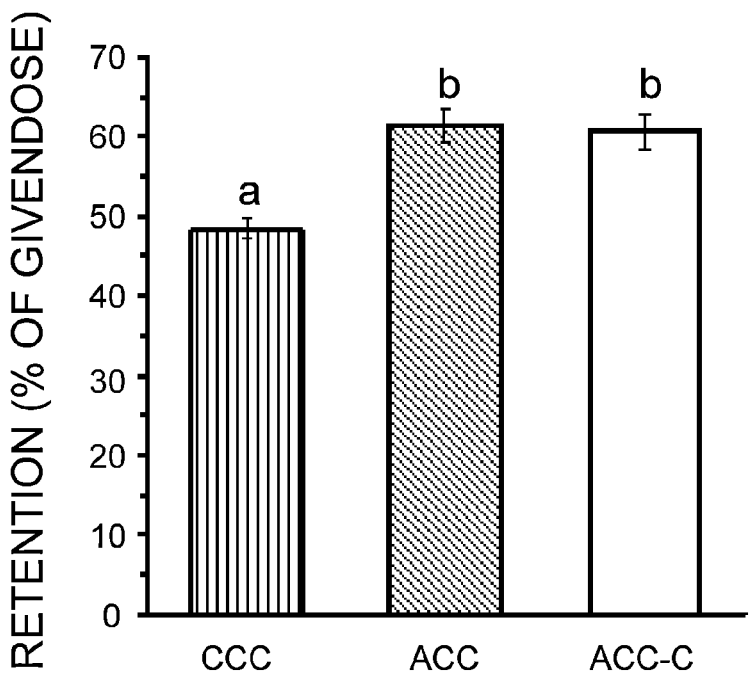
FIG. 39. shows total body retention of calcium following oral administration of radioactive calcium carbonate preparations; from left to right: crystalline calcium carbonate (CCC, n=13), amorphous calcium carbonate (ACC, n=13) and amorphous calcium carbonate with chitosan (ACC-C, n=12). Bars indicate standard error of means (SE). Different superscript letters represent statistical significance (Statistical significance was determined by ANOVA).

Solubility was evaluated by dissolving the different preparations in dilute phosphoric acid. The results shown in FIG. 36 demonstrated that both ACC and ACC-C are more soluble than crystalline calcium carbonate. Fractional absorption was evaluated by intrinsically labeling calcium carbonate preparations with $^{45}Ca$ tracers, orally administrated to male rats using gelatin capsules. The fractional absorption was determined by evaluating [Ca] in the serum, calcium absorption in the femur and by whole body retention over a 34 hour period. Calcium serum analysis revealed that calcium absorption from ACC and ACC-C preparations was up to 40% higher than from crystalline calcium carbonate (FIG. 37), while retention of ACC and ACC-C was up to 26.5% higher than that of CCC (FIG. 39). Absorbed calcium in the femurs of ACC-administrated rats was 30% higher than in CCC treated animals (FIG. 38). While 15% more calcium was absorbed following ACC-C treatment than upon CCC treatment, this difference was not statistically significant. Taken together, these results demonstrate the enhanced solubility and bioavailability of ACC over crystalline calcium carbonate.

The instant invention provides a composition containing ACC and a phosphorylated amino acid or peptide, for example a GAP protein. In an important aspect of the invention, a formulation is provided for treating disorders associated with calcium metabolism or signaling, comprising ACC and a stabilizing amount of phosphorylated amino acid or peptide, for example a GAP protein or its derivatives. The formulation is preferably used for oral administration. The formulation of the invention is used as a therapeutic means, or as a therapeutic supplement, or as a nutritional supplement or as a dietary supplement.

In a preferred embodiment of the invention, ACC prepared according to the invention is comprised in a formulation for treating conditions associated with calcium metabolism or calcium signaling. Said conditions may be selected from the group consisting of bone metabolism disorders, pain, proliferative diseases, neurological disorders, immunologic disorders, cardiovascular diseases, pulmonary diseases, nutritional disorders, reproductive disorders, musculoskeletal disorders, and dental problems. Said treating may comprise mitigating the symptoms of the diseases. Said proliferative disease may be selected from sarcomas, carcinomas, lymphomas and melanomas. Said carcinoma is, for example, breast carcinoma or bronchogenic carcinoma. Said treating may lead to shrinking tumors, stopping their growth, or slowing down or inhibiting the cell proliferation in the tumors. Said pain may be selected from postoperative pain, pain after injury, pain associated with cancer, and neuropathic pain. Said neurological disorder may be selected from demyelinating diseases, dementias, and movement disorders; said disorders being, for example, multiple sclerosis, Alzheimer's disease, Parkinson's disease, or other degenerative disease. Said condition to be treated may comprise a bone or bone marrow disorder, such as fracture or osteoporosis. In a preferred embodiment, a composition of the invention is used for treating a neurodegenerative disorder.

The invention relates to a composition of matter comprising ACC and a stabilizing amount of a phosphorylated amino acid (PAA) or a phosphorylated peptide (PP), for example a composition comprising one or more PAA, or one or more PP such as GAP peptides or their functional fragments, derivatives, or variants. The invention also relates to ACC stabilized with PAA, or PP such as GAPs, for use as a medicament or in the manufacture of a medicament, or for use as a food additive.

The process for the preparation of ACC may comprise the steps:
i) Forming an aqueous solution with calcium ions (with $CaCl_2$ solution).
ii) Addition of soluble or insoluble "additives" (phosphoamino acids, chitosan, chitin, synthetic peptides, phosphorylated peptides/proteins or fragments thereof, etc.).
iii) Addition of carbonate ions (with $Na_2CO_3$ solution or another carbonate source, like for example $CO_2$, or $(NH_4)_2CO_3$).
iv) Agitation.
v) Precipitation of $CaCO_3$ slurry (by centrifugation, filtration etc.).
vi) Slurry dehydration (by lyophilizer, air flow, spray drying etc.).

Analysis of the product may comprise testing the resultant $CaCO_3$ by various methods (as XRD, electron diffraction, SEM) to verify its amorphous nature. Raman spectroscopy (RS) was found to be the most efficient and reliable method to characterize ACC. The Raman shifts characteristics of the mineral reported here are the carbonate peak at 1080 $cm^{-1}$ whose broad shape is indicative of ACC and proportional to its content. The phosphate peak at 950 $cm^{-1}$, is proportional to the phosphate content in the sample. Yet, the ratio between 1080 to 950 $cm^{-1}$ is proportional, but not directly indicative of the $CO_3^{2-}/PO_4^{3-}$ ratio.

Calcium and carbonate ions, in the solutions from which calcium carbonate was precipitated, was usually in the range of from about 10 mM to about 500 mM. The molar ratio of phosphorylated amino acid (PAA) to calcium was usually in the range of 0.01-0.5. A higher concentration of PAA inhibited the spontaneous precipitation. The chitosan, when present, was in the range of 0.03-0.3 wt %.

Peptides which were extracted from demineralized *Cherax* gastroliths by different proteolytic enzymes (trypsin, papain, and *Streptomyces* protease) induced the formation of ACC. It is suggested that phosphoamino acids and phosphopeptides can induce ACC formation and can stabilize it. It is possible that the intact proteins have additional functions. The Raman spectra and EDS analysis show a significant amount of calcium phosphate similar to the ACC induced by total insoluble matrix (ISM), suggesting that the phosphate in the ISM is associated to the proteins.

The precipitated calcium carbonate was checked over long periods for the amorphous/crystalline state. It was found that the samples of ACC obtained by methods of the invention were stable at room temperature for more than seven months, keeping their amorphous state.

EXAMPLES

Example 1

Figure 2C:
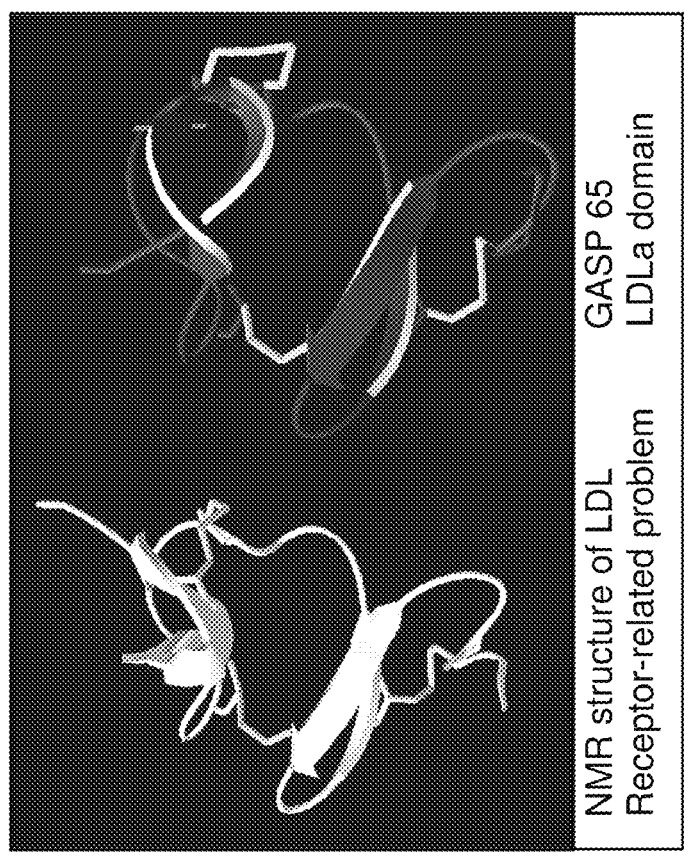

Gastroliths of *Cherax quadricarinatus* were prepared as described [WO 2005/115414]. SDS-PAGE separation of soluble proteins from late premolt gastroliths revealed the presence of at least 6 prominent distinct proteins (FIG. 1A left) with the most abundant being at the size of approximately 65 kDa (gastrolith protein 65, GAP65). Further purification of GAP65 from the entire gastrolith soluble proteins content was performed using DEAE chromatography HPLC with NEWT gradient of up to 1M. GAP65 elution began at 300 mM NaCl but continued mainly at 600 mM (fraction 17). The GAP65 enriched fraction 17 was analyzed by SDS-PAGE and stained with Coomassie (non specific protein staining), "stains all" (negatively charged protein staining), and "pas" (glycoprotein staining), as shown in FIG. 1A right. These staining suggest that GAP65 is the primary protein in this enriched fraction and it is a negatively charged glycoprotein. Trypsin digestion of GAP65 followed by separation using nanospray Qtof2 and sequencing of the peptides using MS-MS generated 7 predicted peptide sequences (FIG. 1B) which were used for the construction of degenerative primers for the acquisition of a complete GAP65 encoded gene sequence based on gastrolith epithelial disc mRNA. FIG. 2A demonstrates the deduced amino acid sequence of GAP65 open reading frame showing a predicted signal sequence of the N-terminus of the protein (bold). Approximately 4.6% of total amino acids of GAP65 were predicted as possible phosphorylation sites (grey boxes), whereas only three predicted N-glycosylation sites (light boxes including three letters), and two predicted O-glycosylation sites (dark boxes at amino acids no. 72 and 173) were found. The negative charge originates in part from the acidic residues aspartic and glutamic acids, which comprise about 12 mol % of the protein. Bioinformatic analysis of GAP65 sequence suggested the presence of three known domains (FIG. 2B): chitin binding domain 2 (ChtBD2) from amino acids 29-102, low-density lipoprotein receptor domain class A (LDLa) from amino acids 122-159, and polysaccharide deacetylase domain from amino acids 195-332. FIG. 2C reveals the predicted 3D structure of the LDLa domain based on the homology to NMR structure of complement-like repeat CR3 from the low density lipoprotein receptor-related protein. This LDLa domain is the only known domain in GAP65 which has a predicted calcium binding property.

Example 2

Figure 3B:
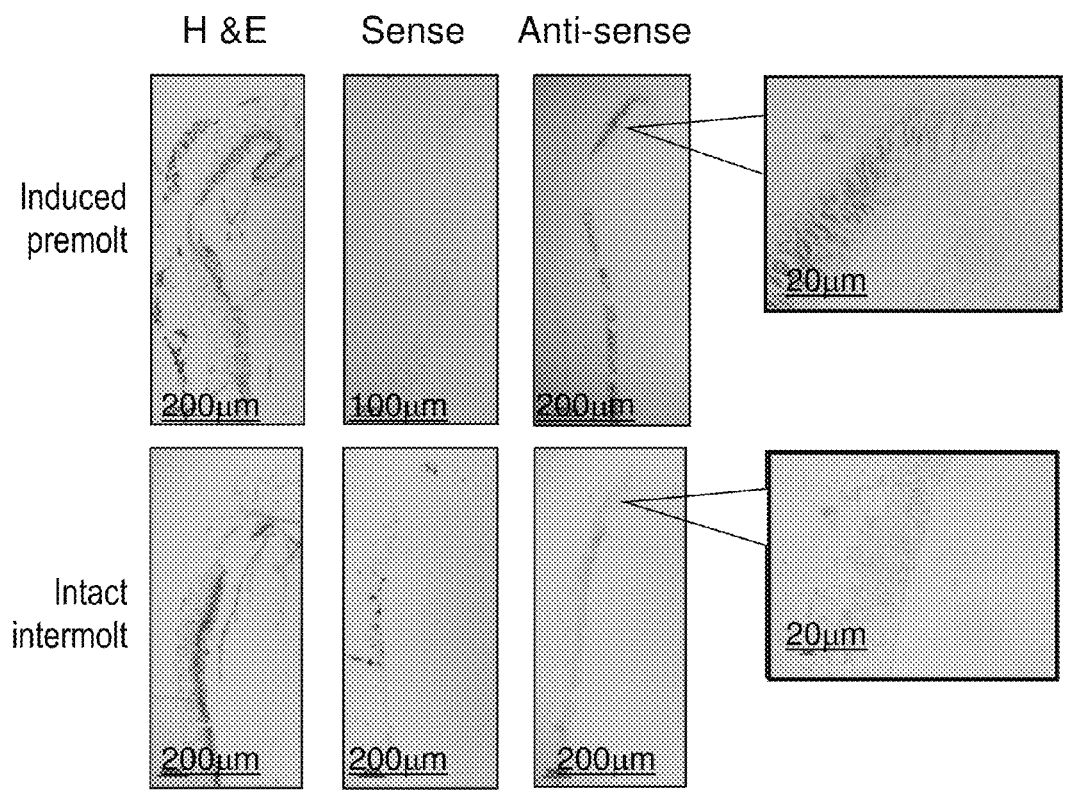
FIG. 3B—localization of GAP65 expression by in situ hybridization in induced premolt and intact intermolt males, left panel represents the hematoxylin and eosin staining (H&E), middle panel represents the negative control sense—GAP65 probe, the two right panels represent the GAP65 anti-sense probe with the last being an enlargement of a specific area, the bar represents 200 μm except for induced premolt sense probe where the bar represents 100 μm.

Specific expression of GAP65 was tested in premolt crayfish in several target tissues by means of RT-PCR (FIG. 3A). The expression of GAP65 was detected in the gastrolith epithelial disc and in the sub-epidermal tissue, both are cuticle related tissues. Expression of GAP65 was not detected in the hepatopancreas, stomach wall, and sperm duct. Localization of GAP65 expression in the gastrolith disc of induced premolt and intact intermolt crayfish by in situ hybridization is presented in FIG. 3B. Left panel represents hematoxylin and eosin staining of the gastrolith disc, middle panel is the control sense probe where no expression is detected. The two right panels represent the anti-sense probe with the last being an enlargement of a specific area. The anti-sense probe reveals that the expression of GAP65 can be detected only in the columnar epithelial cells of the gastrolith disc of an induced crayfish, whereas, in intact intermolt crayfish this expression was not detected.

Example 3

Relative GAP65 transcript levels in the gastrolith epithelial disc following silencing using GAP65 dsRNA were measured using realtime RT-PCR and presented in FIG. 4. GAP65 levels were evaluated in crayfish injected with ecdysone and GAP65 dsRNA, ecdysone and dsRNA carrier, ecdysone and *C. quadricarinatus* vitellogenin (CqVg) dsRNA, and a control injected with both carriers. CqVg, an hepatopancreatic specific gene found mostly in reproductive females, served as a control for sequence specific silencing. Transcript levels of crayfish injected with ecdysone and GAP65 dsRNA were significantly lower than the levels found in the ecdysone and dsRNA carrier injected. In the crayfish injected with ecdysone and CqVg dsRNA, GAP65 transcript levels were similar to the levels detected in the ecdysone and dsRNA carrier injected group. In the control carriers injected crayfish GAP65 transcript levels were higher than the levels found in the ecdysone and GAP65 dsRNA injected crayfish but lower than the levels detected in both the ecdysone and dsRNA injected, and the ecdysone CqVg dsRNA injected crayfish. However, the control carriers group was not statistically significantly different from the three other groups.

Example 4

In order to test the role of GAP65 in gastrolith formation, an RNAi technique using in vivo injections of GAP65 dsRNA to intermolt crayfish was applied. The initiation of gastrolith formation was achieved by injection of ecdysone. In FIG. 5 gastrolith of crayfish injected with either ecdysone+GAP65 dsRNA, ecdysone+dsRNA carrier, or with carriers of both ecdysone and dsRNA can be seen. FIG. 5A is a lateral view of a representative gastrolith dissected from each treatment group. From this image morphological deformities of the gastrolith can be observed in crayfish injected with both GAP65 dsRNA and ecdysone, whereas in crayfish injected with only ecdysone and dsRNA carrier, the gastrolith appeared normal with no deformities. In the control carriers injected the gastrolith appeared undeveloped or in an initial growth stage. FIG. 5B depicts dorsal X-ray view of the crayfish and gastrolith prior to dissection whereas FIG. 5C presents more contrast images of the images of panel B. In crayfish injected with both GAP65 dsRNA and ecdysone, some regions in which less dense detection of mineral is recoded while the gastrolith disc shape structure was retained. In the ecdysone+dsRNA carrier injected crayfish, the gastrolith appeared normal with no effects on mineral densities. The control carrier gastrolith was too small to be detected by the X-ray imaging.

Example 5

Figures 6A, 6B, 6C:
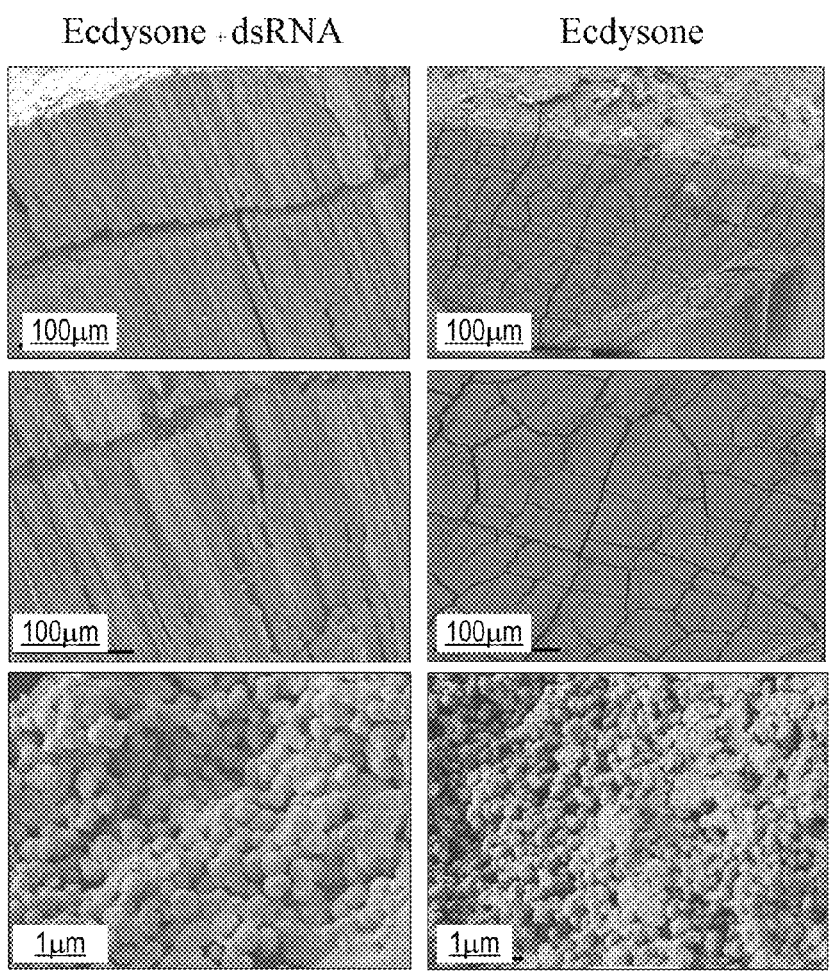
FIGS. 6A and 6B—cross sections of the central part of the gastrolith demonstrating the mineral and matrix arrangement (×50, ×200, respectively)
FIG. 6C—mineral arrangement comprising nano-spherules (×15000); the ecdysone without GAP shows normal gastrolith appearance, while the ecdysone+GAP65 dsRNA treated gastrolith appears deformed.

Scanning electron microscope (SEM) images of gastroliths dissected from crayfish injected with GAP65 dsRNA and ecdysone, and from crayfish injected only with ecdysone and dsRNA carrier, are presented in FIG. 6. FIG. 6A-B depict images of a cross section through the central part of the gastrolith. In gastrolith of crayfish injected with GAP65 dsRNA and ecdysone severe structural abnormalities can be observed when compared with the gastrolith of ecdysone and dsRNA carrier only injected crayfish. The dense mineral layered structure observed in the gastrolith of ecdysone and carrier injected is replaced with a loosely packed columnar mineralization structure, which resembles hollow straws, in the gastrolith of ecdysone and GAP65 dsRNA injected crayfish. The packaging of the ACC in spherules, and the spherules size, is important for the dense packaging of the gastrolith. ×15000 magnification comparing the spherules size between the two treatments is presented in FIG. 6C. In the less densely arranged gastrolith of crayfish injected with ecdysone and GAP65 dsRNA spherule size ranged between approximately 100-300 nm whereas in the normal ACC deposited in gastrolith of crayfish injected with ecdysone and dsRNA carrier the spherules have narrower size distribution, ranged from 40-60 nm.

Example 6

Figure 7A:
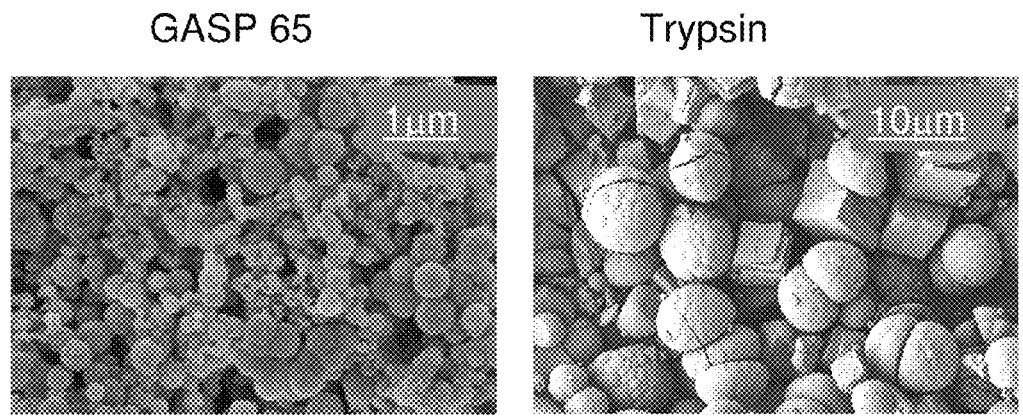
FIG. 7A—calcium carbonate precipitate with GAP65 enriched fraction (left), calcium carbonate precipitated with equivalent amount of trypsin as a control (right)
Figure 7B:
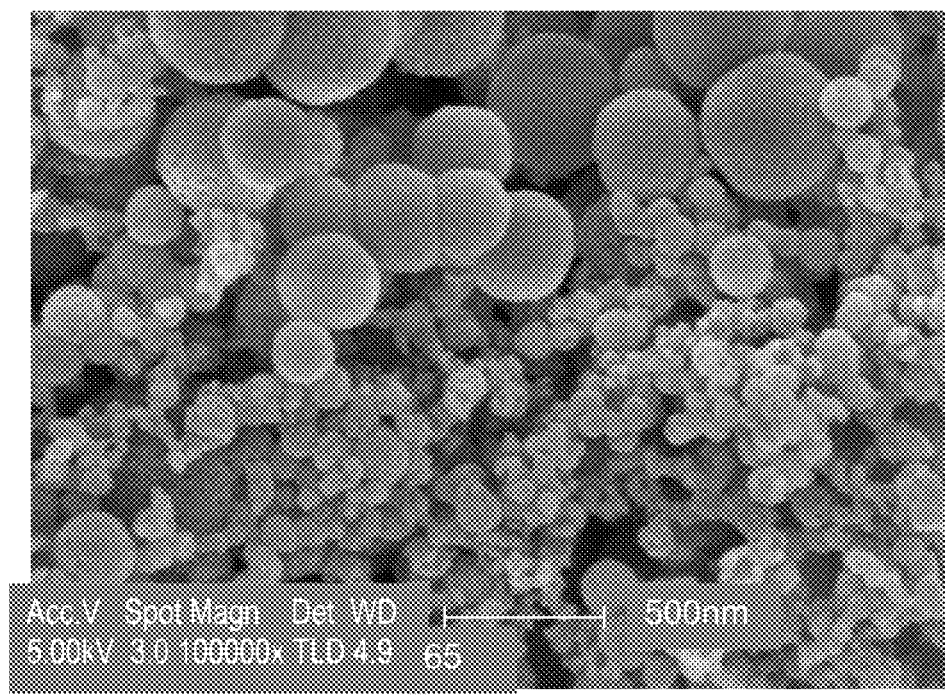

In order to elucidate the role of GAP65 in the biomineralization process, an in vitro calcium carbonate precipitation essay testing the stabilization of ACC was established. FIG. 7 presents precipitation results of calcium carbonate in the presence of GAP65 and in the presence of other protein (trypsin). SEM images in FIG. 7A indicate the distinct polymorph of calcium carbonate in each treatment. Precipitation of calcium carbonate in the presence of GAP65 resulted in the deposition of an amorphous form (ACC), observed as a thin layer comprised of 100-500 nm spherules. Precipitating experiments performed under the same conditions but in the presence of trypsin resulted with rapid crystallization, observed as large 10 µm single crystals of calcite and vaterite spherulites. FIG. 7B confirms the nature of the ACC in calcium carbonate precipitated in the presence of GAP65. Raman analysis is showing the distinct spectra of ACC with a clear broad peak at 1070 cm$^{-1}$. The presence of GAP65 in the ACC spherules formed by the in vitro precipitation was confirmed by purification of the protein from the mineral fraction of the precipitate and its evaluation by SDS-PAGE against the original GAP65 enriched fraction.

Example 7

Figure 8A:
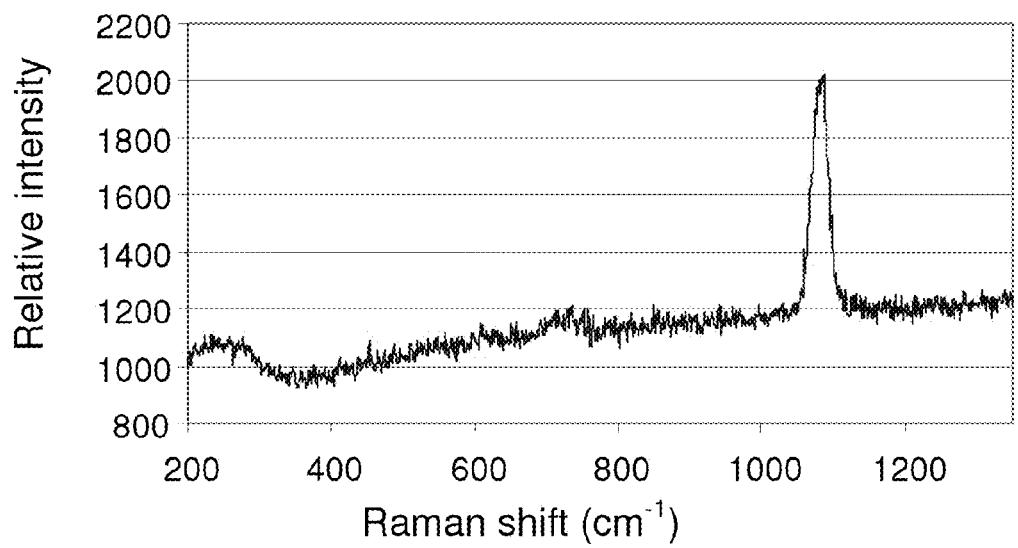
FIG. 8A—Raman spectra of calcium carbonate obtained by precipitation with GAP65 enriched fraction.
Figure 8B:
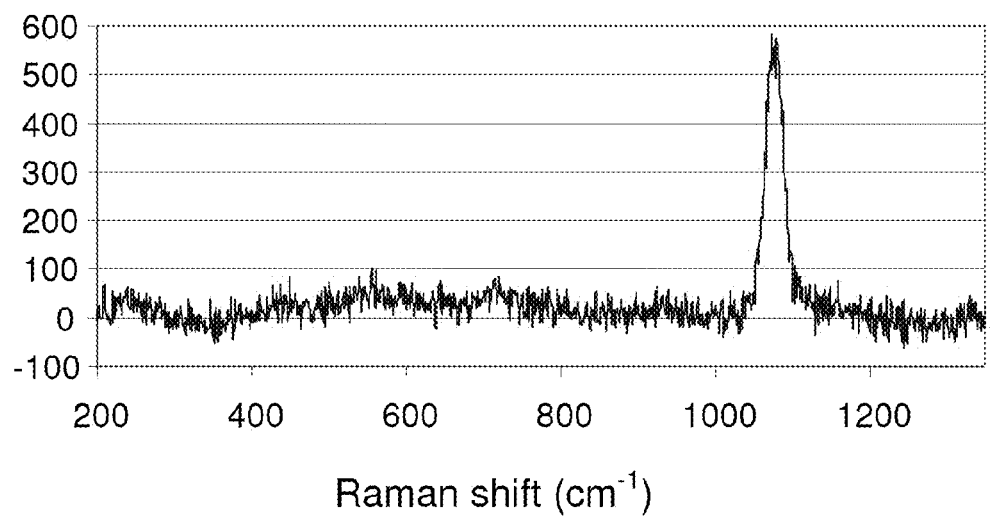
Figure 9A:
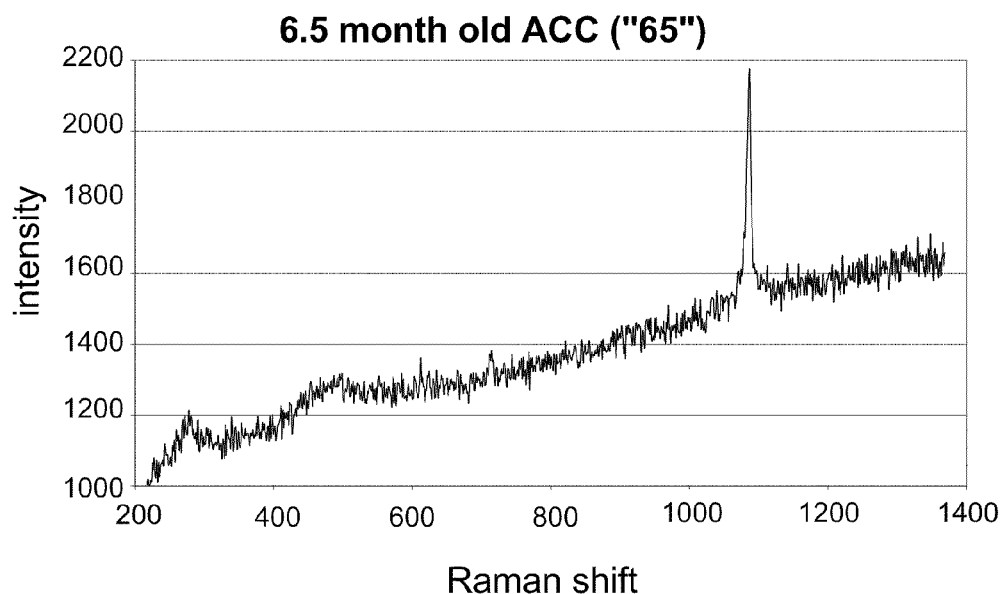
FIG. 9A—shows Raman spectra of the ACC obtained by precipitation with GAP65 enriched fraction 6.5 month after the precipitation.
Figure 9B:
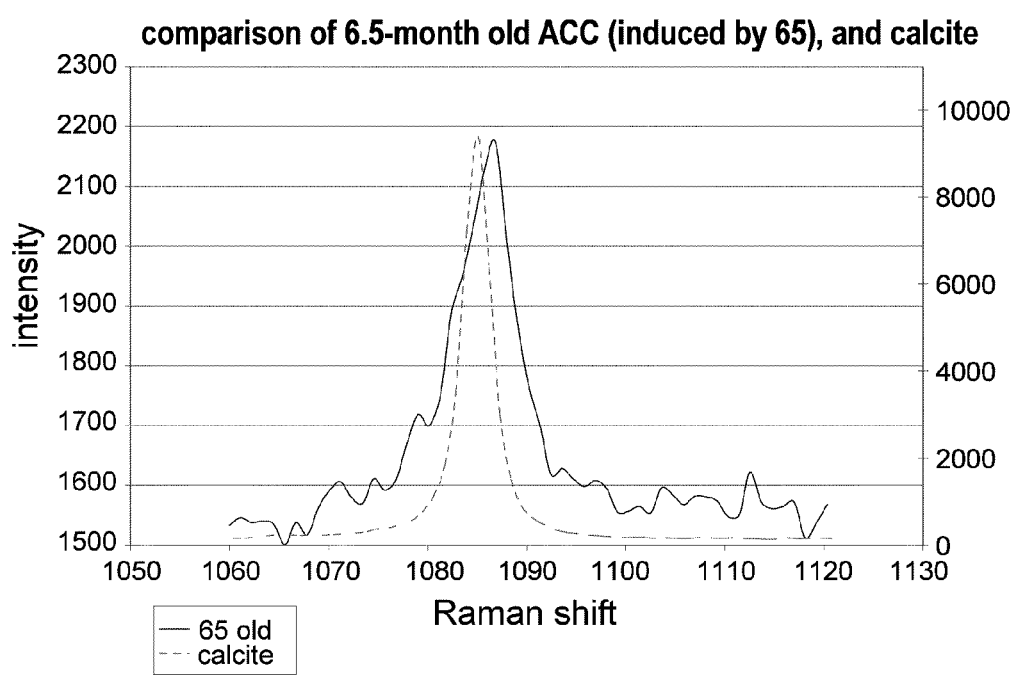
FIG. 9B is a comparison of the Raman spectra (around the 1085 peak) of 6.5-month old ACC (induced by GAP65) with calcite.
Figure 10A:
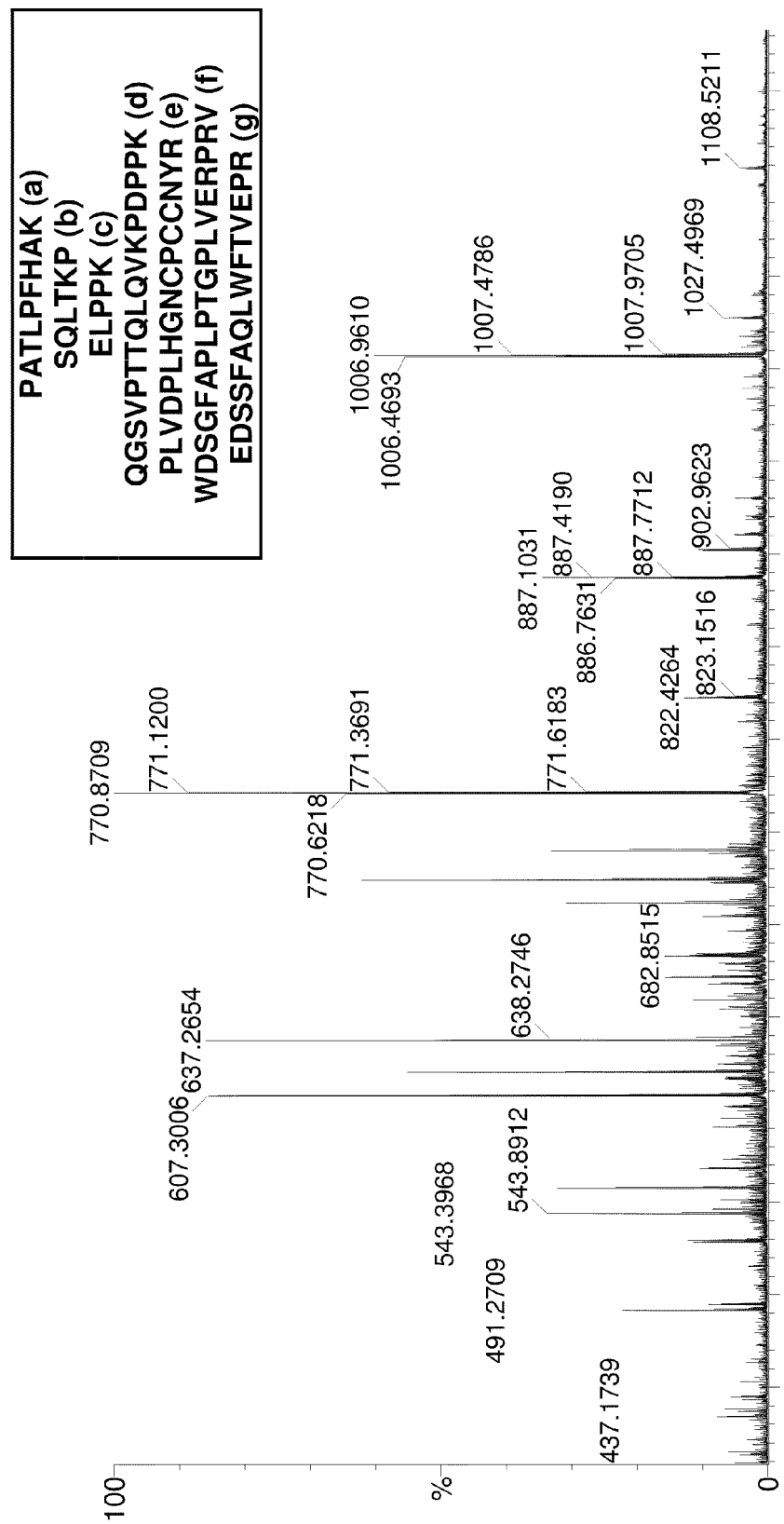
FIG. 10A shows GAP22.
Figure 10B:
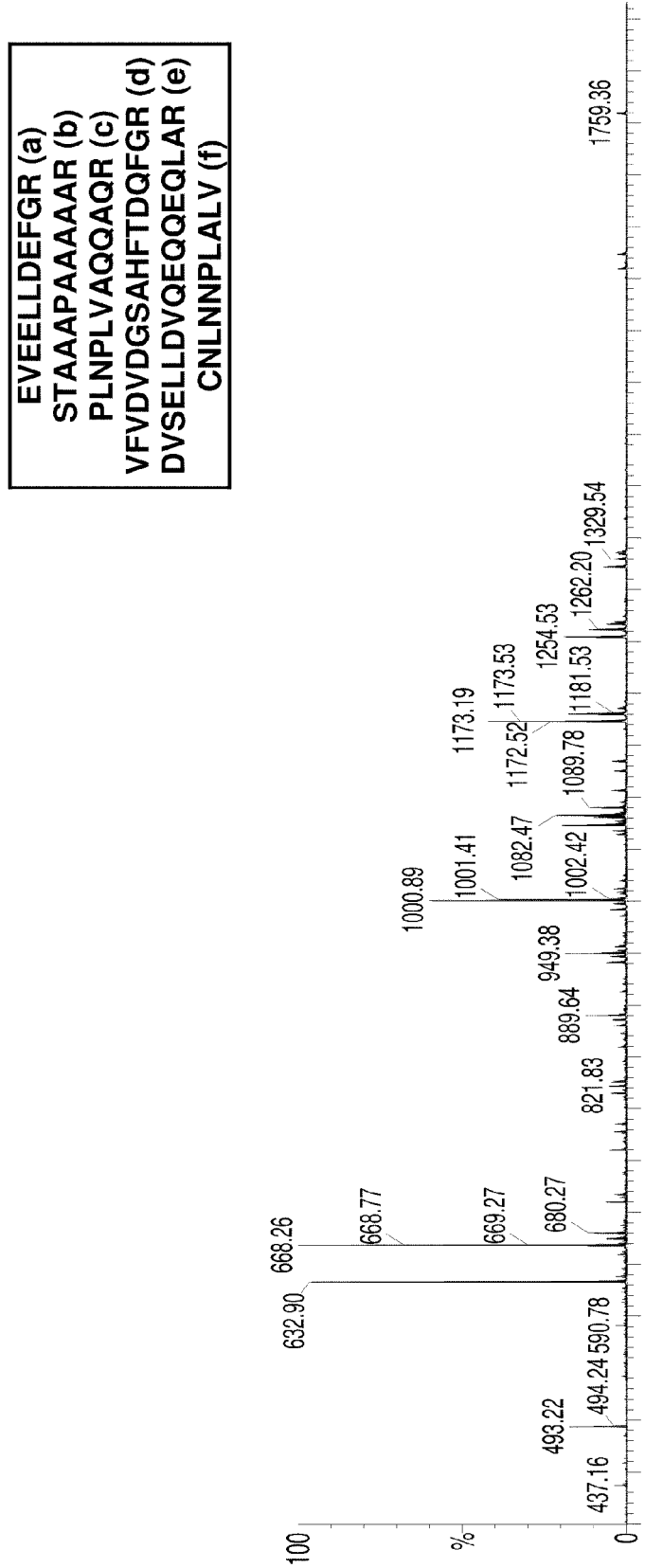
FIG. 10B shows GAP21.
Figure 10C:
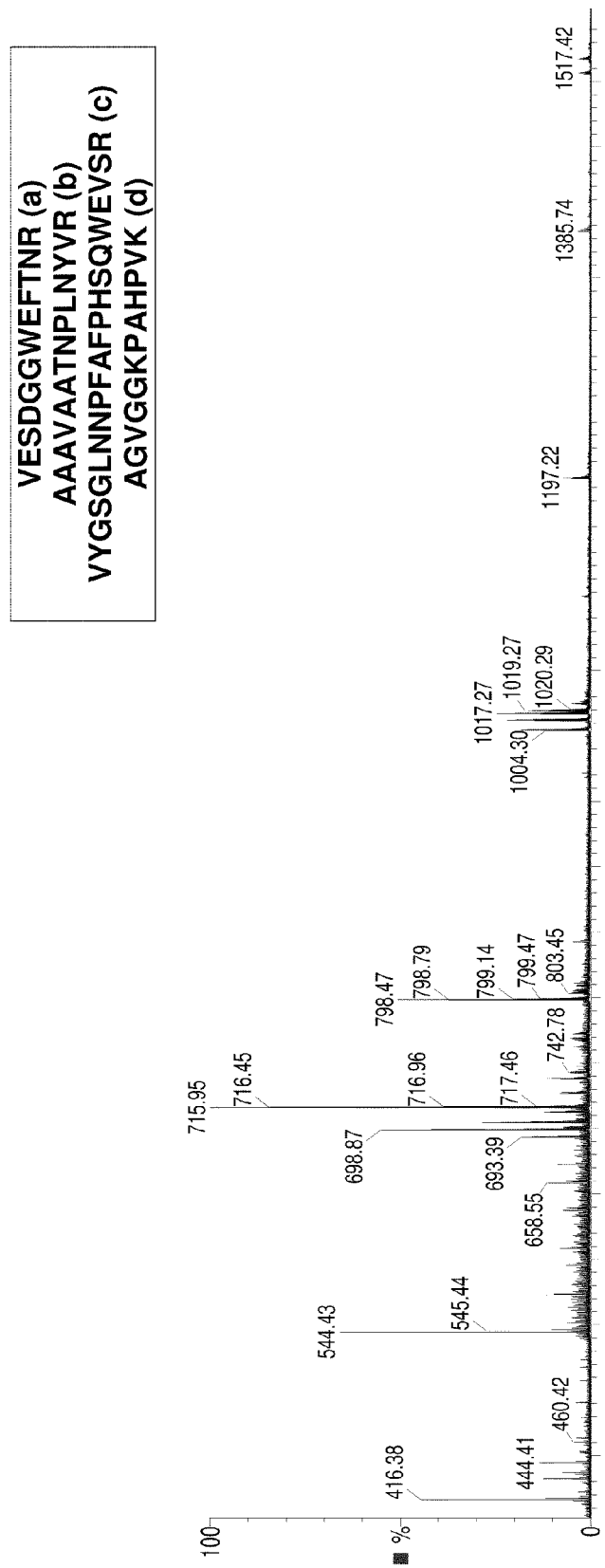
FIG. 10C shows GAP12.

The stability of ACC precipitated with GAP65 was tested by Raman spectroscopy in the samples held at room temperature. 100 µl of 1M $CaCl_2$ was added to 10 ml double distilled water (final concentration: 10 mM). 80 µl from the protein extraction solution (1.2 µg/µl) were added (final concentration ~10 µg/ml). 100 µl of 1M $Na_2CO_3$ (final concentration: 10 mM) was added following an intensive shaking. The vial was centrifuged for 5 min at 4000 rpm, the precipitate was smeared over a glass slide and instantly dried with air flow. The $CaCO_a$ deposits were initially characterized by polarized microscope as a mixture of calcite, vaterite, and ACC. The observations were confirmed by Raman spectroscopy. The ACC was in a form of a thin "crust", and it was estimated to comprise about at least 50% of the total $CaCO_3$. The ACC remained stable at room temperature for at least 1 months, as Raman spectra of the ACC one day after precipitation, 27 days after precipitation, and 6.5 month after precipitation show (FIGS. 8A, 8B, 9A). Comparison of the Raman spectra (around the 1085 peak) of 6.5-month old ACC with calcite (FIG. 9B) indicated mixture seemingly comprising ACC and vaterite (when considering a shoulder on the 1085 peak possibly being an onset of peak splitting characterizing vaterite).

Example 8

The gastrolith extract inhibits calcium carbonate crystallization and stabilizes the amorphous form of calcium carbonate (ACC). ACC was detected by Raman spectrometry in a precipitate of $CaCO_3$ prepared from a solution containing $CaCl_2$, $Na_2CO_3$ and the gastrolith extract (FIG. 11). The presence of ACC is validated by the presence of a predominant broad peak at about 1080 cm$^{-1}$. The peak at 560 is attributed to the glass substrate. Expressions of the GAP genes were found to be specific to the gastrolith epithelial disc and sub-epidermal tissue, both are cuticle related tissues. Specific expression of GAP21, GAP22 and GAP65 in several target tissues was checked by means of RT-PCR, similarly as described in Example 2. GAP21 and GAP65 expressions were found in both cuticle related tissues. GAP22 expression was found only in the gastrolith epithelial disc. The cDNA sequences of the corresponding genes were obtained and their deduced proteins were found (FIGS. 13-15). All four proteins were found to contain signal peptides at their N-terminus (underlined amino acids in FIGS. 13-15 and bold in FIG. 2). Similarity search against databases of conserved domains revealed that GAP65 contains three conserved domains; Chitin-binding domain 2, Low density lipoprotein receptor domain class A and Polysaccharide deacetylase domain. GAP12, GAP21 and GAP22, on the other hand, show no significant similarity to any known domain.

Blast alignment of GAP12 and GAP21 revealed a 46.3% identity in the deduced amino acid sequences of these proteins (FIG. 15B).

Physico-chemical analysis of the deduced proteins revealed, that the calculated molecular weights of GAPs 12, 21 and 65 are smaller than expected, 9.9, 19.5 and 60.8 kDa respectively, while that of GAP22 is higher than expected, 28.6 kDa (Table 1, FIG. 12), GAP12, GAP21 and GAP65 have an acidic pI, therefore they are negatively charged at the physiological pH of the gastrolith (near pH 8.5). GAP12 and GAP21 have a high percentage of non-polar, aliphatic amino acids (glycine, alanine and valine) and a high percentage of the polar but uncharged amino acid proline (highlighted in gray in Table 1). GAP65 has a high content of acidic amino acids, but no other distinguishable characteristic. GAP22 has a basic pI, therefore it is positively charged at the physiological pH of the gastrolith. Its main characteristics are a high percentage of the polar but uncharged amino acid proline and of the positively charged arginine. According to bioinformatic analysis, GAP 12 and 21 show some similarities in amino acid composition to other proteins known to be involved in calcium precipitation in crustaceans.

Example 9

Figure 16:
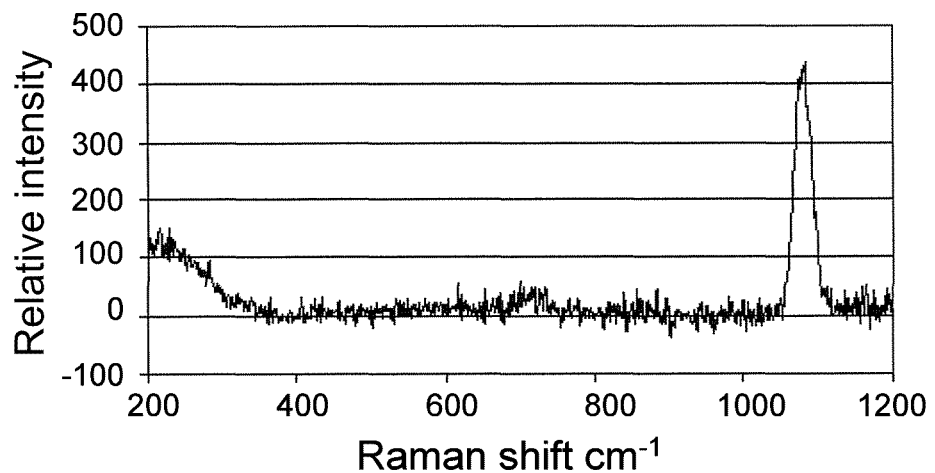
Figure 28:
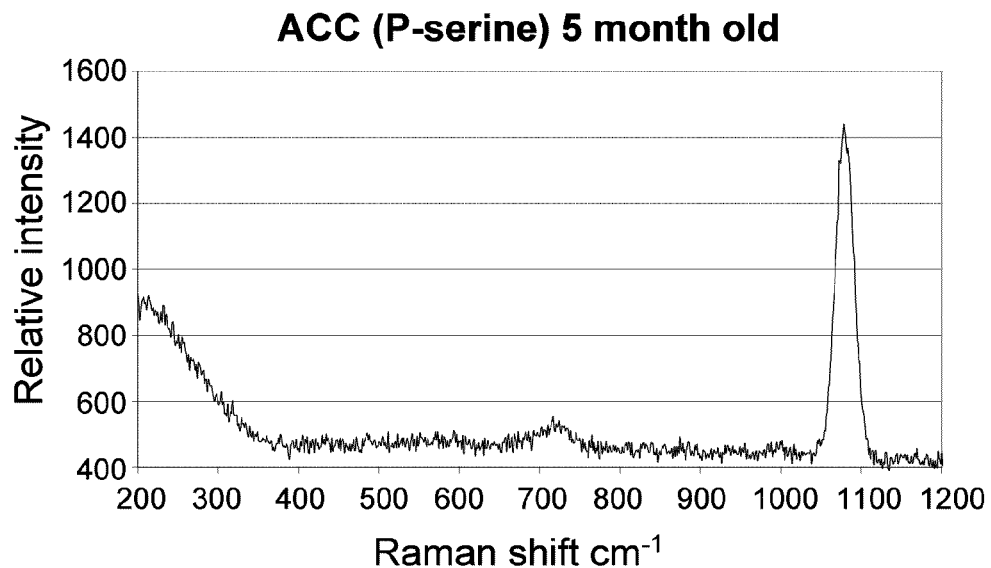
FIG. 28 to FIG. 32 show Raman Spectra of samples prepared according to Examples 9, 10 and 18-20, respectively, which were stored after the precipitation at room temperature as described.

100 µl of 1M $CaCl_2$ were added to 10 ml double-distilled water (DDW), attaining the final concentration of 10 mM. 200 µl of P-serine (P-Ser) solution (100 mM) were added to the solution, attaining 2 mM of P-Ser. 100 µl of 1M $Na_2CO_3$ (final concentration: 10 mM) were added following an intensive shaking. The vial was centrifuged for 5 min at 4000 rpm at room temperature. The upper solution was removed and the precipitation was smeared over a glass slide and instantly dried by air flow. RS showed ACC (FIG. 16). The sample was stored at room temperature and tested for ACC stability five months after the precipitation (FIG. 28).

Example 10

Figure 17:
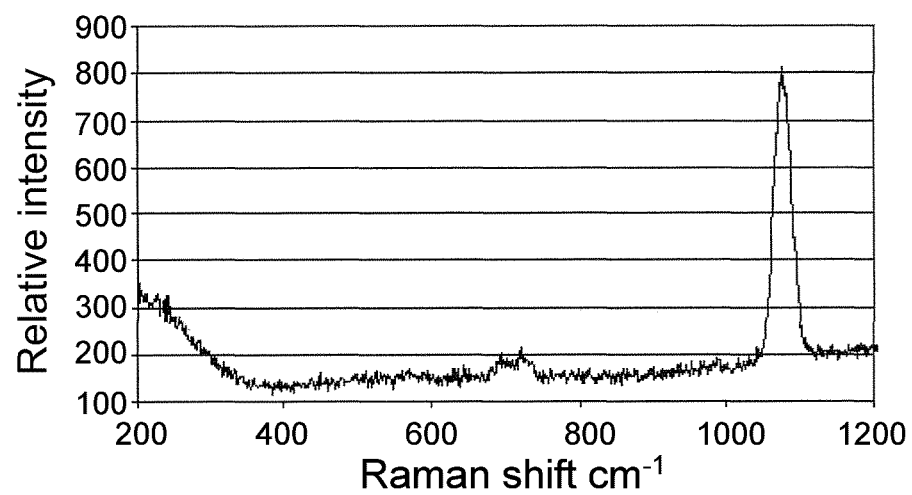
Figure 29:
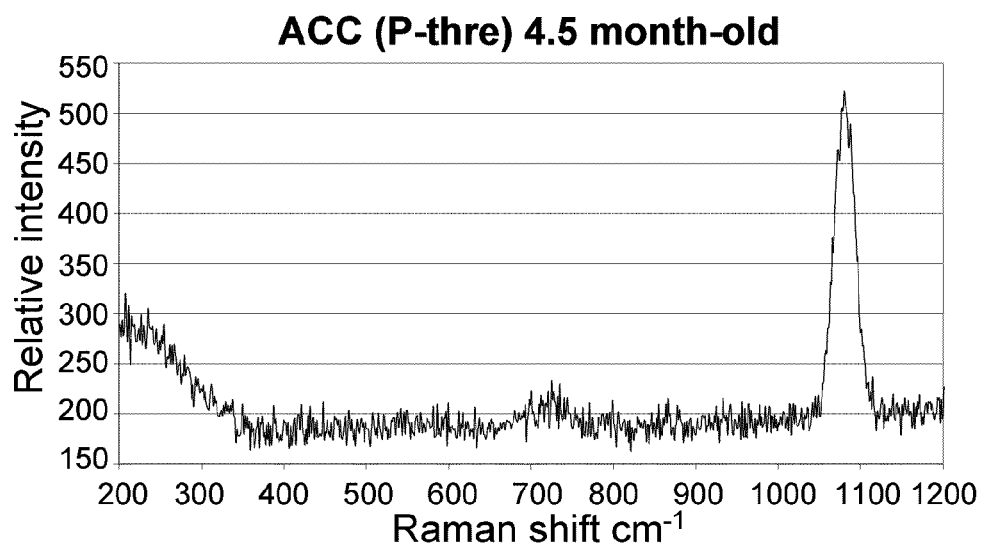

100 µl of 1M $CaCl_2$ were added to 10 ml DDW (final concentration: 10 mM). 100 µl of P-threonine (P-Thr) solution (100 mM) were added to the solution, attaining 1 mM P-Thr. 100 µl of 1M $Na_2CO_3$ (final concentration: 10 mM) were added following an intensive shaking. The vial was centrifuged for 5 min at 4000 rpm at room temperature. The upper solution was removed and the precipitation was smeared over a glass slide and instantly dried by air flow. RS showed ACC (FIG. 17). The sample was stored at room temperature and tested for ACC stability 4.5 months after the precipitation (FIG. 29).

Example 11

Figure 18:
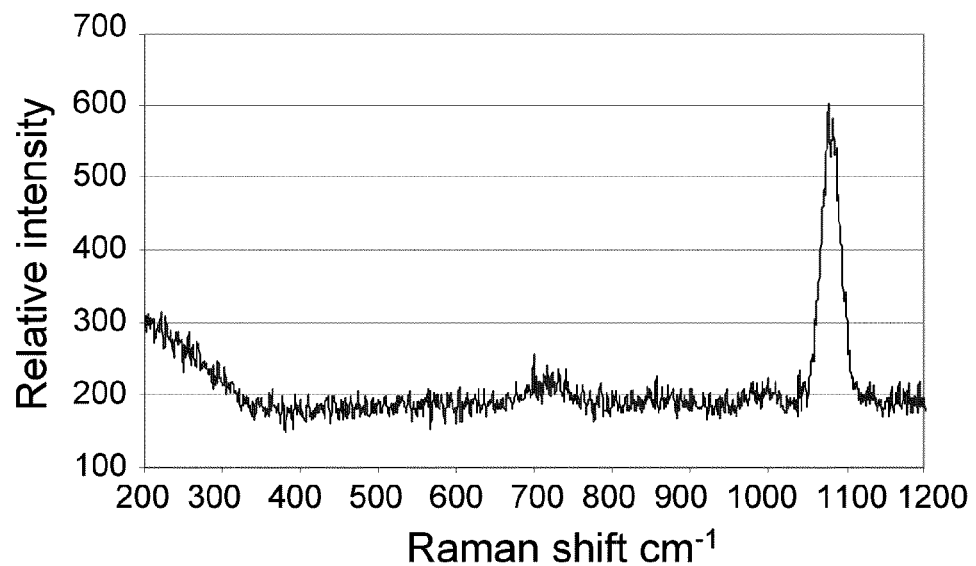

100 µl of 1M $CaCl_2$ were added to 10 ml DDW (final concentration: 10 mM). 200 µl of P-serine solution (100 mM) were added to the solution. 100 µl of 1M $Na_2CO_3$ (final concentration: 10 mM) were added following an intensive shaking. The vial was centrifuged for 5 min at 4000 rpm at room temperature. The upper solution was removed and the precipitation was frozen in liquid nitrogen and freeze dried in a lyophilizer. RS showed ACC (FIG. 18).

Example 12

Figure 19:
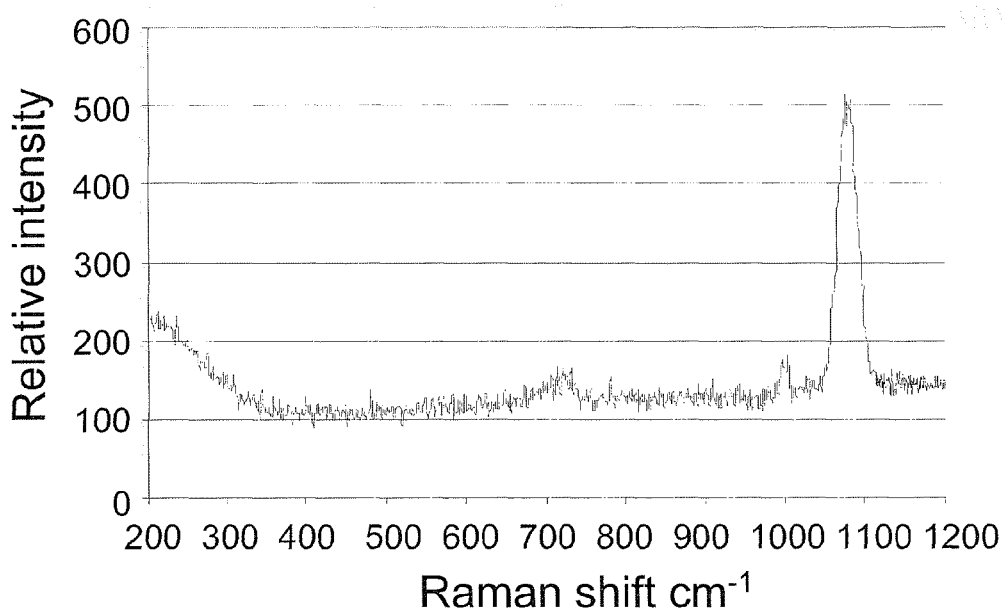

The conditions as described in Example 11 were modified by changing the final concentrations of $CaCl_2$ and $Na_2CO_3$ from 10 mM to 100 mM. RS showed ACC (FIG. 19).

Example 13

Figure 20:
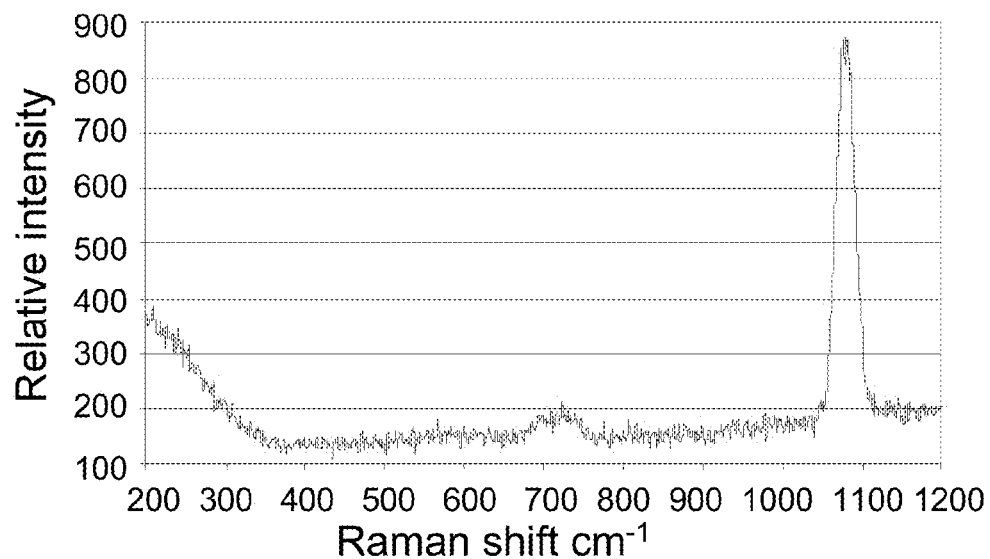

The conditions as described in Example 10 were modified by changing the dehydration method from flowing air to lyophilizing, RS showed ACC (FIG. 20).

Example 14

Figure 21:
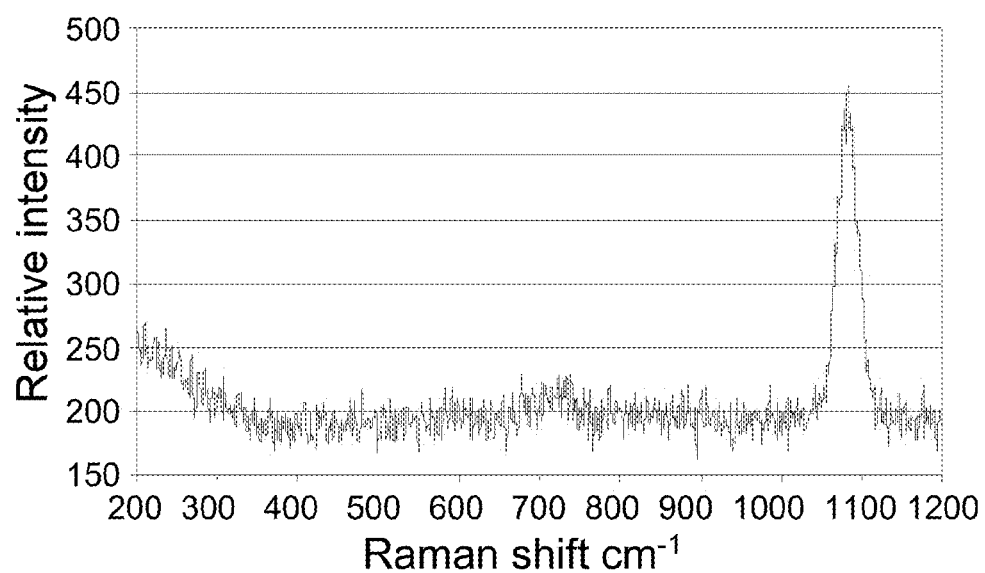

A system comprising 20 mM $CaCl_2$, 20 mM $Na_2CO_3$, 2 mM P-Ser with chitosan (3 wt % Dissolved in 0.2 M acetic acid) that was added to the precipitation solution, after the calcium addition to a final concentration of 0.3 wt %. RS showed ACC (FIG. 21).

Example 15

Figure 22:
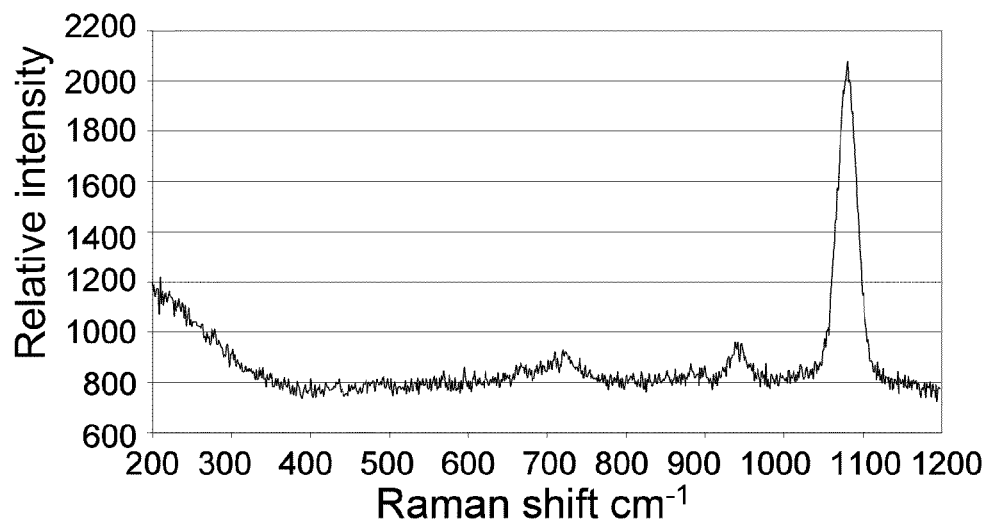

The conditions as described in Example 14 were modified by employing the final concentrations of 0.5 M $CaCl_2$, 0.5 M $Na_2CO_3$, and 3 mM P-Ser. This composition represents the upper concentration limit. RS showed ACC (FIG. 22).

Example 16

Figure 23:
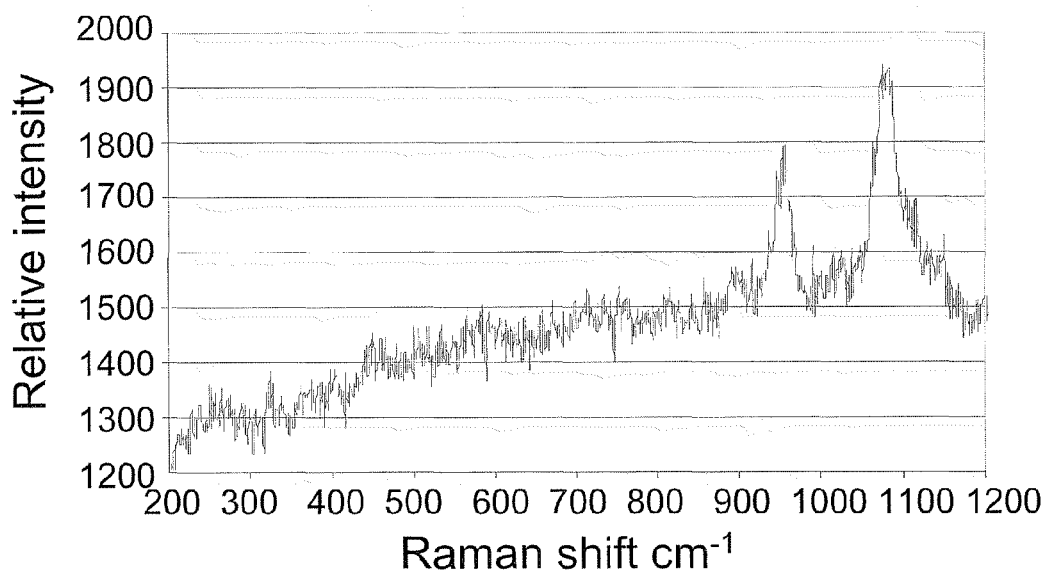

Gastroliths were dissected from endocrinologically-induced premolt crayfish, weighed, rinsed with distilled water and kept at −20° C. After the external layer of the gastrolith was scraped to eliminate any residual external material, the gastroliths were frozen using liquid nitrogen and ground to powder using a mortar and pestle. Demineralization was performed by stirring of each gram of gastrolith powder was in 20 ml of 0.02 M ammonium acetate, 0.5 M EGTA, pH 7.0, on ice. When the $CaCO_3$ dissolution completed, the suspension was centrifuged (2000 rpm, 15-20 min, 4° C.) and the supernatant was collected. The residual insoluble matrix (ISM) was used as additive to the calcifying solution (step ii). 200 µl of the ISM (estimated: ~30 µg protein) were added to 10 ml of the crystallization mixture comprising 10 mM $CaCl_2$ and 10 mM $Na_2CO_3$, followed by air flow dehydration. RS showed ACC (FIG. 23).

Example 17

Figure 24:
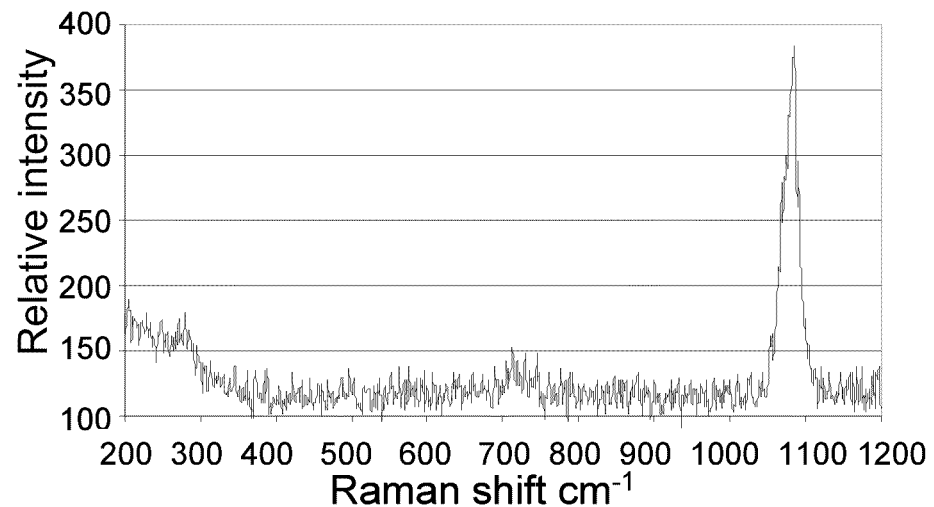

The conditions as described in Example 16 were modified by changing the final concentrations of $CaCl_2$ and $Na_2CO_3$ from 10 mM to 20 mM, and the volume of ISM to 100 μl (~15 μg protein), while dehydrating by means of lyophilizing. RS showed ACC (FIG. 24).

Example 18

Figure 25:
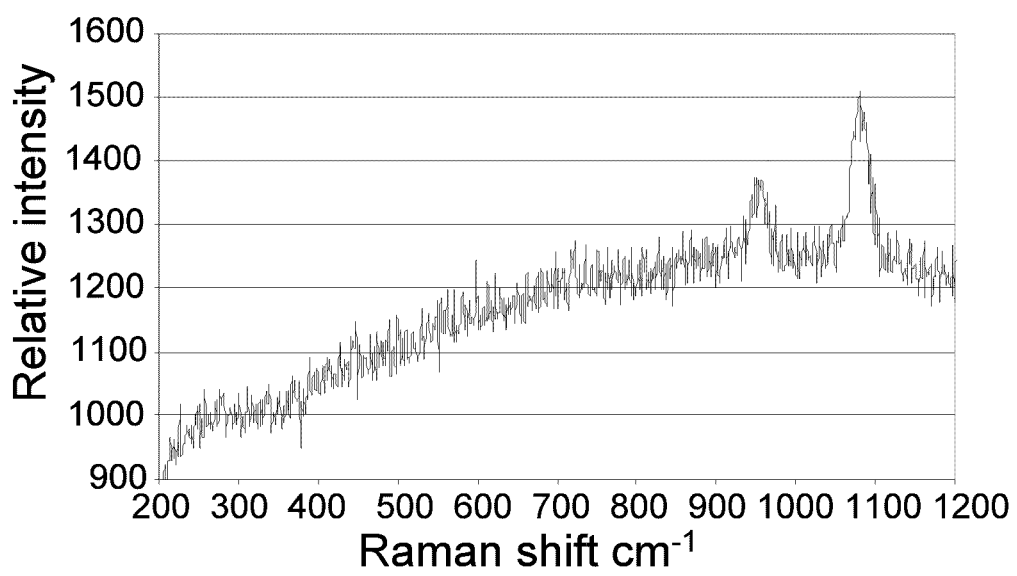

The ISM was treated with various proteolytic enzymes in order to release the chitin binding proteins (either hydrogen or covalent bonding) from the chitinous insoluble phase, and to demonstrate the activity of resulting peptides in ACC induction and stabilization (FIG. 25).

Figure 30:
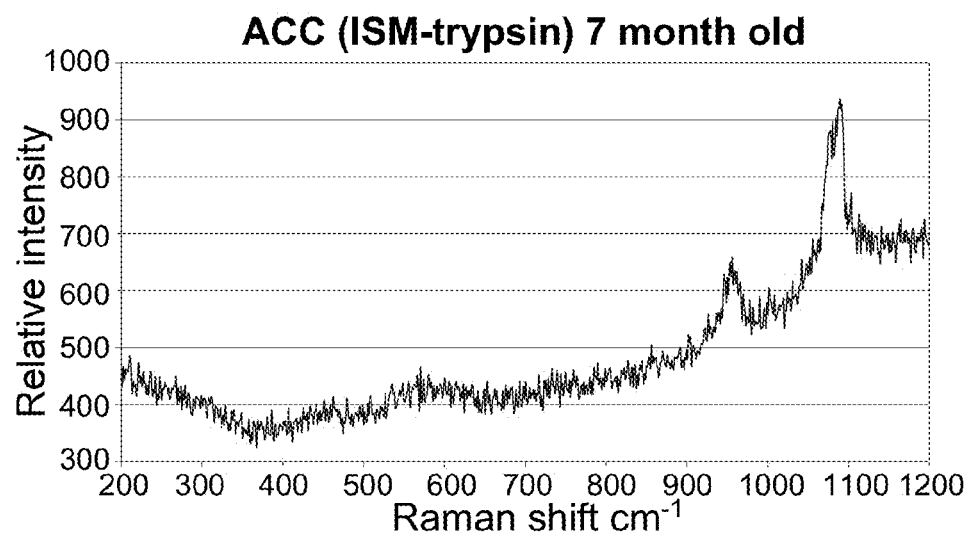

28 ml of ammonium acetate (2 mM) were added to 7 ml of ISM. From this solution 10 ml were mixed with 10 ml of trypsin (3.8 mg/ml) in ammonium acetate (2 mM). The suspensions of the ISM with the proteolytic enzymes were incubated for 2 hr at 4° C. under vortexed condition. After the incubation the vials were centrifuged for 5 minutes at 4000 rpm. The supernatant which contained the ISM digested proteins was removed; 1 ml of the supernatant (equivalent to 100 μl of insoluble matrix and to ~150 μg protein was added to 10 ml of $CaCl_2$ (10 mM). 100 μl of 1M $Na_2CO_3$ (final concentration: 10 mM) were added following an intensive shaking. The vial was centrifuged for 5 min at 4000 RPM, the precipitation was smeared over a glass slide and instantly dried with air flow. RS showed ACC (FIG. 25). The sample was stored at room temperature and tested for ACC stability seven months after the precipitation (FIG. 30).

Example 19

Figure 26:
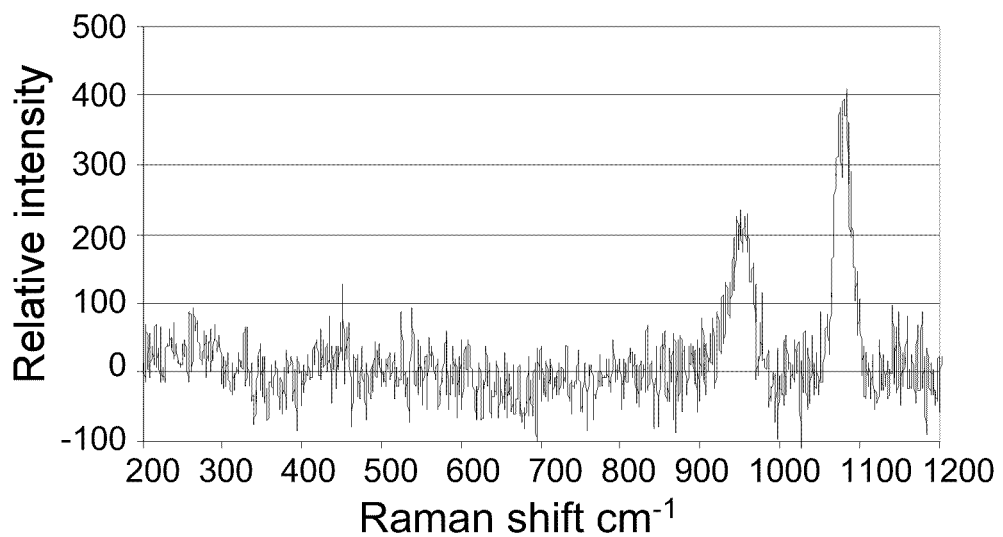
Figure 31:
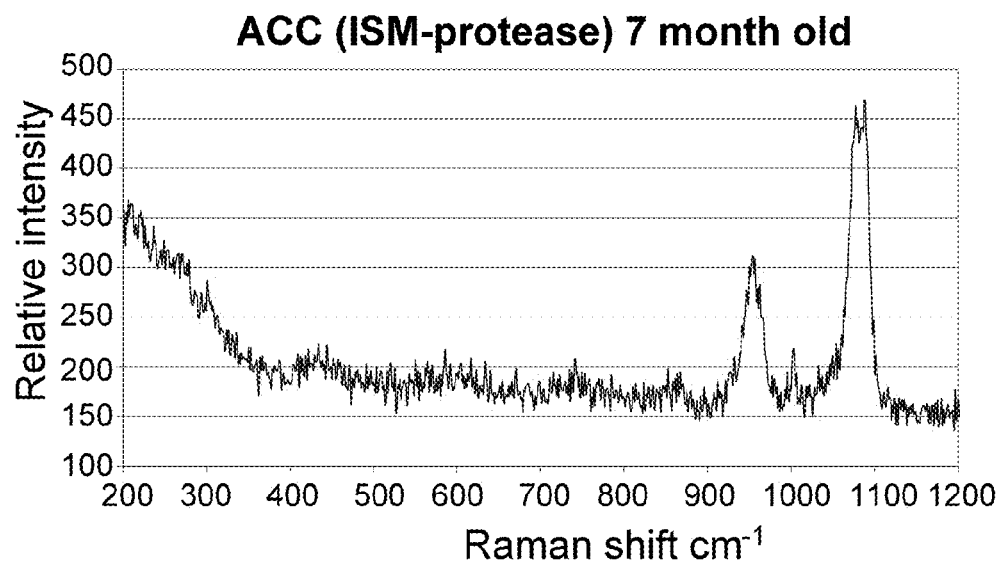

28 ml of ammonium acetate (2 mM) were added to 7 ml of ISM. From this solution 10 ml were mixed with 10 ml of protease from *Streptomyces griseus* (Sigma P6911, 0.6 mg/ml) in ammonium acetate (2 mM). The suspensions of the ISM with the proteolytic enzymes were incubated for 2 hr at 4° C. under vortexing. After the incubation the vials were centrifuged for 5 minutes at 4000 rpm. The supernatant which contained the ISM digested proteins was removed; 1 ml of the supernatant was added to 10 ml of $CaCl_2$ (10 mM). 100 μl of 1M $Na_2CO_3$ (final concentration: 10 mM) were added following an intensive shaking. The vial was centrifuged for 5 min at 4000 RPM, the precipitation was smeared over a glass slide and instantly dried with air flow. RS showed the ACC peak (at 1080), and additional secondary peak, possibly of calcium phosphate (peak at 950) (FIG. 26). The sample was stored at room temperature and tested for ACC stability seven months after the precipitation (FIG. 31).

Example 20

Figure 27:
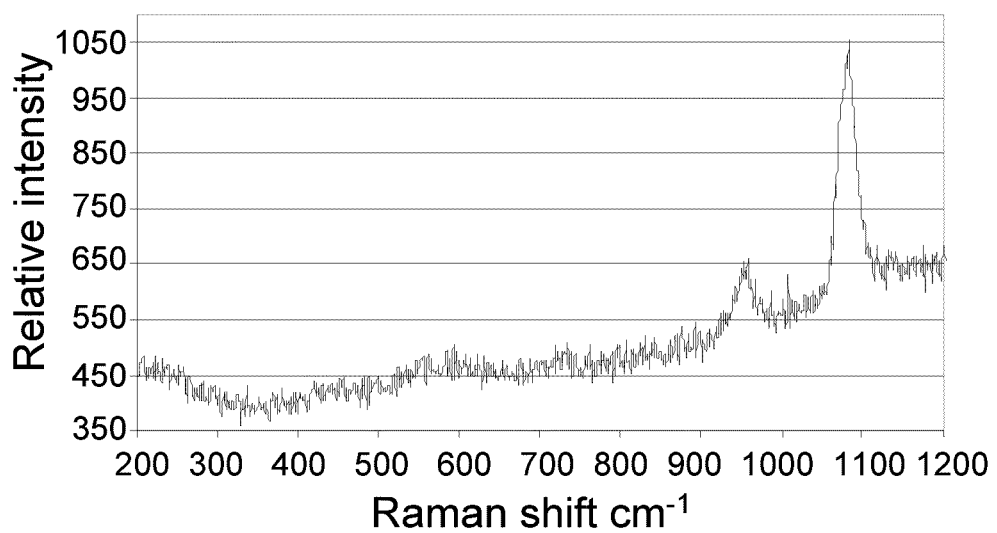
Figure 32:
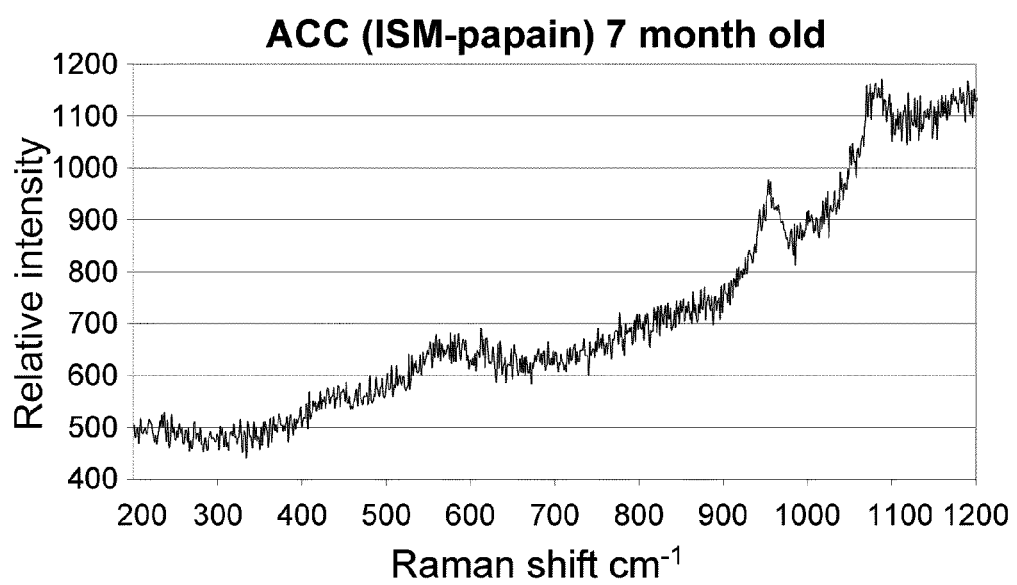

28 ml of ammonium acetate (2 mM) were added to 7 ml of ISM. From this solution 10 ml were mixed with 10 ml of papain (0.26 mg/ml) in ammonium acetate (2 mM). The suspensions of the ISM with the proteolytic enzymes were incubated for 2 hr at 4° C. under vortexed condition. After the incubation the vials were centrifuged for 5 minutes at 4000 rpm. The supernatant which contain now the ISM digested proteins was removed; 1 ml of the supernatant was added to 10 ml of $CaCl_2$ (10 mM). 100 μl of 1M $Na_2CO_3$ (final concentration: 10 mM) were added following an intensive shaking. The vial was centrifuged for 5 min at 4000 RPM, the precipitation was smeared over a glass slide and instantly dried with air flow. RS showed ACC, and possibly calcium phosphate (FIG. 27). The sample was stored at room temperature and tested for ACC stability seven months after the precipitation (FIG. 32).

Example 21

Stable amorphous calcium carbonate (ACC) was synthesized by mixing two water based solutions: a 0.2M $CaCl_2$ and 0.2M $NaCo_3$ containing also 1.2 mM of Phosphoserine. Into the ACC-C samples a 3% (by weight) chitosan solution dissolved in 0.2M Acetic acid was added during mixing to reach a maximum concentration of 20%. Mixing of the two solution generated an immediate precipitation of Amorphous calcium carbonate that was instantly filtered and dried to maximum moisture of 5%. Crystalline calcium carbonate (CCC) was synthesized by mixing 0.1 M $CaCl_2$ solution with 0.1 M $Na_2CO_3$ in 0.3 M TRIS solution set to pH 9. The suspension was stirred at 40° C. for two hours. The CCC slurry was filtered using a Buchner funnel and washed twice with Absolute ethanol.

Example 22

Figure 33A:
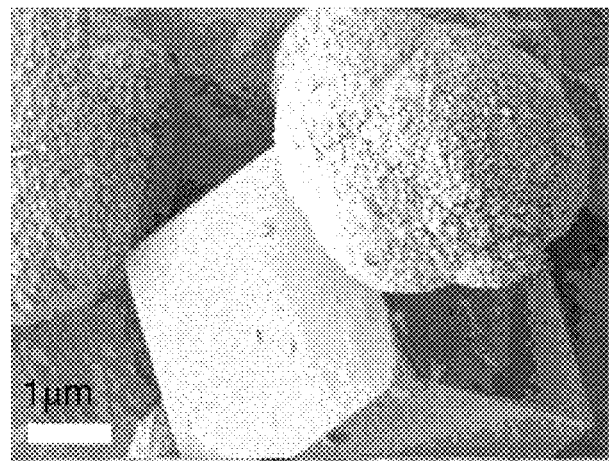
FIG. 33A shows crystalline calcium carbonate (CCC) magnification ×15,000.
Figure 33B:
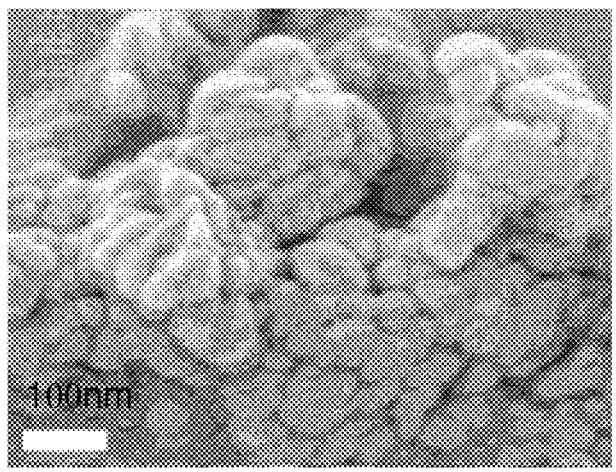
FIG. 33B shows amorphous calcium carbonate (ACC) magnification ×100,000.
Figure 33C:
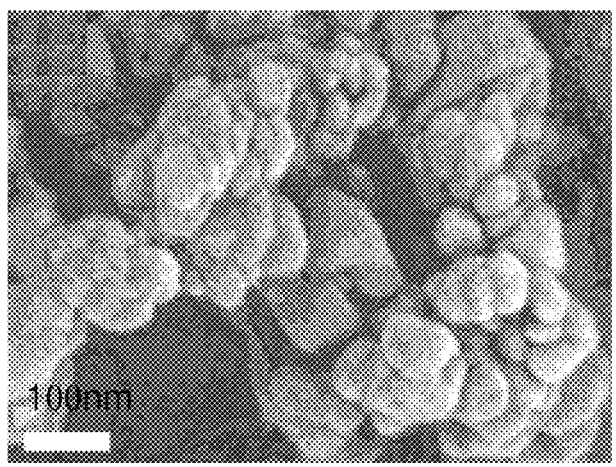
FIG. 33C shows amorphous calcium carbonate with chitosan (ACC-C) magnification ×100,000. Bars represent scale.

High resolution scanning electron microscope (HR-SEM) images representing morphology differences of three collected calcium carbonate preparations of Example 21, namely crystalline calcium carbonate (CCC), amorphous calcium carbonate (ACC) and amorphous calcium carbonate with chitosan to (ACC-C) are presented in FIG. 33. CCC consists of a mixture of two crystalline forms (FIG. 33A): calcite (rhombic) and vaterite (spherules) both ranging from 1-10 μm particles. The observed spherules contain smaller nano-sized crystallites, a formation which together with its 1-10 μm size is typical to vaterite. The ACC particles (FIG. 33B) are 1-2 orders of magnitude smaller than the calcite and vaterite crystals (FIG. 33A) which increases the materials effective surface area by up to 1×106. The amorphous nature of ACC is depicted by its 40-100 nm particles with varying morphologies. ACC-C embedded on a chitosan matrix (FIG. 33C) also appears as 40-100 nm particles with varying morphologies. ACC and ACC-C can not be differentiated using HR-SEM, it appears that the chitosan matrix of ACC-C is covered by ACC particles and therefore invisible in the SEM images.

Example 23

Figure 34:
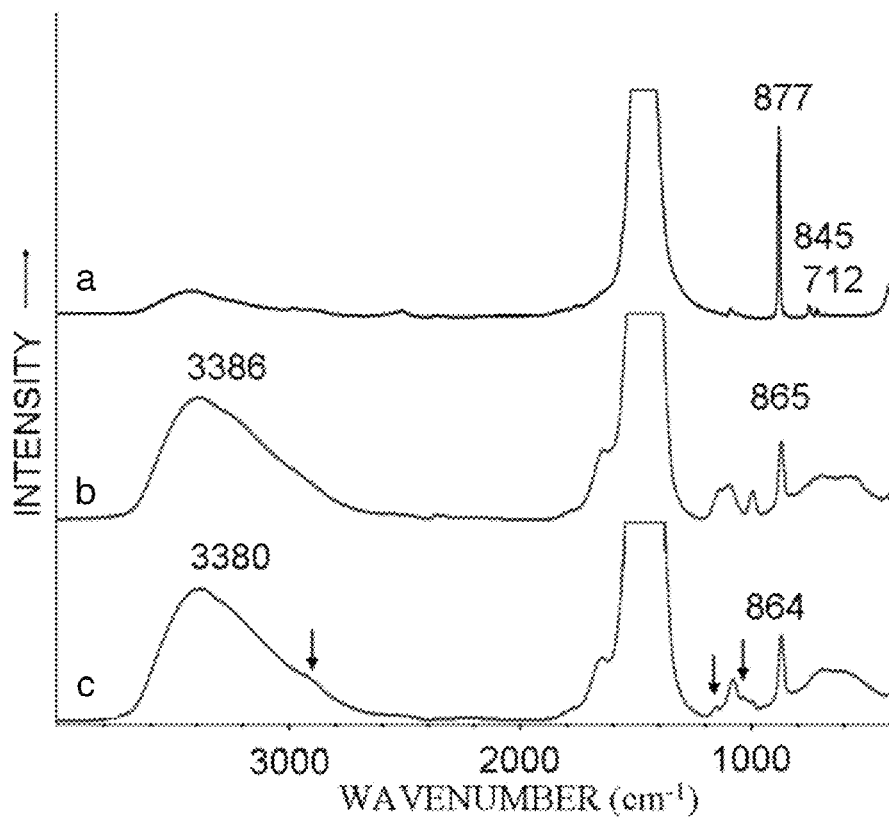
FIG. 34. shows Fourier Transformed Infrared spectroscopy (FTIR) of the three calcium carbonate preparations.
Figure 35:
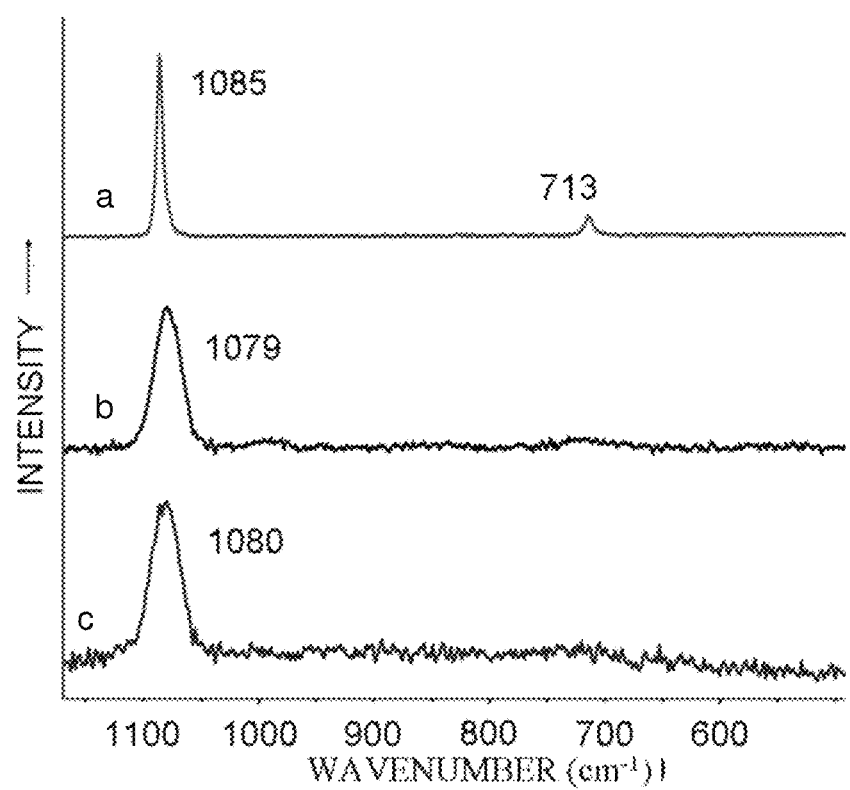
FIG. 35. shows Raman spectroscopy of the three calcium carbonate preparations.

The polymorphic nature of the three calcium carbonate preparations of Example 21 was determined by Fourier Transform Infrared (FTIR) spectroscopy (FIG. 34). The carbonate vibrations shifts from one polymorph to another allow affirmation of the polymorph based on the wavenumber of the vibrations.

The CCC preparation spectrum reveals the presence of calcite represented by a sharp peak at ~870 $cm^{-1}$ and a peak at ~712 $cm^{-1}$. Vaterite presence was detected according to a vibration ~745 $cm^{-1}$ (FIG. 34a). The presence of both calcite and vaterite in the CCC preparation is supported also by the SEM image in FIG. 33. The spectrum of the ACC preparation show the nature of amorphous calcium carbonate characterized by a typical broad peak at ~865 $cm^{-1}$ (FIG. 34b). The spectrum of the ACC-C preparation with a broad peak at ~864 $cm^{-1}$ also suggests the presence of amorphous calcium carbonate (FIG. 34c). The presence of chitosan in the ACC-C preparation was verified by peaks at 1028 cm$^{-1}$, 1150 cm$^{-1}$ and 2877 cm$^{-1}$ that were previously identified in the FTIR spectrums of clean chitosan (indicated by arrows).

Example 24

Raman spectra of the three calcium carbonate preparations of Example 21 was preformed. Raman analysis of the CCC preparation (FIG. 35a) with a sharp peak at 1085.6 cm$^{-1}$ and a small peek at 713.3 cm$^{-1}$ represents the presence of calcite, while vaterite is not visible in this spectrum because of the high intensity of the major calcite peak which masks the vaterite peak that typically appears as a doublet at 1087 cm$^{-1}$. The ACC preparation is characterized by a broad Raman peek at 1079.8 cm$^{-1}$ showing the presence of amorphous calcium carbonate (FIG. 35b). Similarly, the ACC-C preparation presents a broad peak at 1080.4 cm$^{-1}$ (FIG. 35c). Chitosan, present in the ACC-C preparation, does not produce a known peak in Raman spectroscopy, however a distinctive background reading was obtained during measurement of ACC-C, possibly caused by the presence of chitosan in the sample.

Example 25

Solubility of ACC, ACC with chitosan (ACC-C) and crystalline calcium carbonate (CCC) as described in Example 21 was evaluated by dissolving the different preparations in dilute phosphoric acid. The results presented in FIG. 36 demonstrate that both ACC and ACC-C are more soluble than crystalline calcium carbonate. both ACC and ACC-C's final pH were higher than the final pH observed for calcite by more than 1 pH unit, which is a 20% increase (p<0.05). Both ACC and ACC-C's final pH was higher than the final pH of the CCC preparation by more than 0.5 pH units, a 9% increase.

Furthermore (Table 2), it took commercial calcite 49 seconds to reach 50% of the maximum pH, while it took 20, 21 and 22 seconds for CCC, ACC-C and ACC, respectively. In all the tested samples a remnant precipitate was still present at the end of the analysis.

TABLE 2

Dissolution parameters

| Calcium carbonate preparation | pH$_{MAX}$ | T$_{50\%}$ (s) |
|---|---|---|
| Calcite | 5.11 ± 0.02$^a$ | 49$^a$ |
| CCC | 5.64 ± 0.01$^b$ | 20$^b$ |
| ACC | 6.46 ± 0.14$^c$ | 22$^b$ |
| ACC-C | 6.51 ± 0.21$^c$ | 21$^b$ | pH$_{MAX}$ represents the final pH that was reached after 240 seconds (pH$_{MAX}$ results are presented as means±SE). T$_{50\%}$ represents the time it took the pH to reach 50% of its maximum value. Different superscript letters represent statistical significance (Statistical significance was determined by ANOVA). These results support the notion that the solubility of calcium salts affects its bioavailability.

Example 26

Bioavailability experiments testing the fractional absorption of ACC, ACC-C and CCC of Example 21 was evaluated by intrinsically labeling calcium carbonate preparations with $^{45}$Ca tracers, orally administrated to male rats using gelatin capsules. The fractional absorption was determined by evaluating [Ca] in the serum, calcium absorption in the femur and by whole body retention over a 34 hour period.

Fifty one two month old male Wistar rats were fed ad libitum laboratory rat chow pellets adequate in nutrients and had free access to water for 48 hours. Four days before the beginning of the experiment the regular diet was replaced with low calcium diet containing 0.24±0.05% calcium (0.675±0.05% phosphate) specially prepared by mixing two food types, 0.01% calcium (0.3% phosphate) and 1% calcium (0.8% phosphate). The two food types were separately grounded in a mill to yield two powders which were dry mixed in a ratio of 4:1 respectively until fine homogenization. The homogenized powder was extruded to form new food pellets.

Seventeen hours prior to capsule administration, the rats were weighed and blood samples were taken (baseline). The rats were then placed into individual metabolic cages and deprived of food and water until 3 h post-capsule administration. A single capsule containing a specific calcium carbonate preparation prepared according to Example 21 (CCC, ACC, or ACC-C, n=17 in each group) was administered intragastrically to each of the experimental rats. Three hours and 24 hours post dosing ~10 g of low calcium food pellets (0.01% calcium) were given to each rat. Distilled water was allowed ad libitum starting from three hours post-capsule administration.

Serum Ca

Blood samples were taken from each rat's tail vein 17 hours prior to the capsule administration (time 0) and 2, 3, 6, 10, 24 and 34 hours post administration. FIG. 37 presents the changes in [Ca] in the serum as calculated by the radioactive readings normalized to the administered dose ([serum cpm× total calcium dose]/[total cpm×the volume of the sample]). The C$_{max}$ values in rats that received ACC were significantly higher (up to 40%) than in the CCC group (FIG. 37 and Table 3). The C$_{max}$ values in rats that received ACC-C were also higher (up to 12%) than in rats that received CCC, but this difference was not statistically significant (Table 3). The pharmacokinetic analysis indicates that the bioavailability of the ACC and ACC-C is significantly higher than that of the CCC (AUC values are higher by 22.5% and 20%, respectively, p<0.05) while the time to reach the maximal concentration (T$_{max}$) did not differ between groups (Table 3).

TABLE 3

Pharmacokinetic parameters of calcium in the Serum following oral administration of radioactive calcium carbonate preparations

| Compound | C$_{max}$ (μg/mL) | T$_{max}$ (h) | AUC$_\infty$(μg × h/mL) |
|---|---|---|---|
| CCC | 5.8 ± 0.7$^a$ | 3.0 ± 0.3$^a$ | 109.7 ± 6.4$^a$ |
| ACC | 8.1 ± 0.8$^b$ | 2.8 ± 0.2$^a$ | 134.5 ± 7.0$^b$ |
| ACC-C | 6.5 ± 0.6$^{ab}$ | 3.4 ± 0.2$^a$ | 131.5 ± 9.7$^b$ |

Different superscript letters represent statistical significance (p<0.05, Statistical significance was determined by ANOVA).

Femur Ca

Thirty four hours post-dosing the rats were sacrificed. The right and left femurs were removed and dried at 70° C. in an oven overnight. Each femur was weighed and then separately decalcified in a decalcifying solution. Radioactivity of the samples was measured and the calcium content was normalized according to each preparations specific radioactivity and calcium dose and then calculated per 100 mg dry bone content ([total femur cpm×total calcium dose]/[total cpm×femur weight]×100). Calcium content in the femurs of rats that received ACC was 30% higher (p<0.05) then that in rats that received CCC. The calcium content in the femurs of rats that received ACC-C were 15% higher than that in the rats that received CCC, but these changes were not statistically significant. The advantageous bioavailability of amorphous constructs is demonstrated by the femur analysis, which suggests that calcium from ACC and ACC-C is more effectively incorporated in the bone relative to calcium from CCC. This result shows a correlation between the elevated calcium levels detected in the serum to the high levels detected in the femur.

Total Body Retention of Ca

Feces and urine were collected during the 17 hours of starvation in the acclimation period (baseline) and during the entire 34 hours of the experiment. Radioactivity of the urine and feces samples was measured, and the retention values were calculated by subtracting the radioactivity measured in the feces and urine from the given dose ([Intake−Feces and urine excretion]/Intake×100). The retention values presented in FIG. 39 suggest that rats that received CCC-containing capsule retained 48.5±1.3% of the received dose, whereas rats that received ACC and ACC-C-containing capsules retained 61.4±2.0% and 60.6±2.1% of the received dose, respectively. This corresponds to a significant increase by 26.6% and 25%, respectively, as compared to the retention in the CCC group (p<0.05).

While this invention has been described in terms of some specific examples, many modifications and variations are possible. It is therefore understood that within the scope of the appended claims, the invention may be realized to otherwise than as specifically described.

---

The invention claimed is:

1. An orally administrable composition comprising stable amorphous calcium carbonate (ACC) and at least one phosphorylated amino acid selected from phosphorylated serine and phosphorylated threonine, wherein said phosphorylated amino acid stabilizes the amorphous form of calcium carbonate, wherein the molar ratio of said phosphorylated amino acid to calcium is in the range of 0.006-0.5, and wherein said composition is formulated for oral administration.

2. A pharmaceutical formulation comprising the orally-administrable composition according to claim 1 and further comprising fillers or solvents or additives.

3. The pharmaceutical formulation according to claim 2, wherein the additives comprise chitin or chitosan.

4. A method of treating a bone disorder, a bone marrow disorder or an injury, comprising orally administering a formulation comprising the composition of claim 1.

5. The method according to claim 4, wherein the bone disorder is osteoporosis.

6. The method according to claim 4, wherein the injury is a fracture.

7. A nutraceutical formulation or food additive or functional food, comprising the orally-administrable composition of claim 1 and further comprising fillers or solvents or additives.

8. A dietary supplement comprising the orally-administrable composition according to claim 1 and further comprising fillers or solvents or additives.

9. A method of treating a condition selected from the group consisting of pain, proliferative diseases, neurological disorders, immunologic disorders, cardiovascular diseases, pulmonary diseases, nutritional disorders, reproductive disorders, musculoskeletal disorders, degenerative diseases, and dental problems, comprising orally administering a formulation comprising the orally administrable composition of claim 1.

10. The method according to claim 9, wherein the proliferative disease is breast carcinoma or bronchogenic carcinoma.

11. The method according to claim 9, wherein the pain is selected from postoperative pain, pain after injury, pain associated with cancer, and neuropathic pain.

12. The method according to claim 9, wherein the neurological disorder is selected from demyelinating diseases, dementias, and movement disorders.

13. The method according to claim 9, wherein the degenerative disease is selected from multiple sclerosis, Alzheimer's disease, and Parkinson's disease.

14. The method according to claim 9, wherein the degenerative disease is a neurodegenerative disorder.

15. A method of preparing the orally administrable composition of claim 1, comprising mixing in aqueous phase in any order a soluble salt comprising calcium, a carbonate source and at least one phosphorylated amino acid selected from phosphorylatedserine and phosphorylated threonine.

* * * * *

SEQUENCE LISTING

```
<160> NUMBER OF SEQ ID NOS: 28

<210> SEQ ID NO 1
<211> LENGTH: 548
<212> TYPE: PRT
<213> ORGANISM: Cherax quadricarinatus

<400> SEQUENCE: 1

Met Ile Arg Arg Val Thr Thr Pro Leu Leu Ala Leu Leu Leu Ala Gly
1               5                   10                  15

Trp Val Val Ala Gln Thr Thr Asp Met Asp Pro Glu Gln Tyr Cys Ala
            20                  25                  30

Arg Arg Asp Asp Glu Tyr Phe Arg Lys Asp Phe Gly Asp Pro Ala Glu
        35                  40                  45

Phe Ala Ser Asp Tyr Arg Ala Asn Cys Gly Val Tyr Tyr Arg Cys Val
    50                  55                  60

Pro Ala Pro Ala Gly Lys Arg Ser Ile Ser Ala Ser Gln Cys Gln Ser
65                  70                  75                  80

Glu Leu Phe Phe Asp Val Gln Gln Gln Ile Cys Glu Arg Lys Ser Lys
                85                  90                  95

Val Thr Asn Cys Glu Gln Ile Asp Lys Glu His Pro Pro Gln Pro Phe
            100                 105                 110

Trp Pro Leu Arg Glu Gly Glu Glu Ser Gln Cys Lys Ser Gly Glu Ile
        115                 120                 125

Met Cys Gly Ser Gly Glu Cys Leu Pro Gln His Arg Phe Cys Asp Glu
    130                 135                 140

Asn Ser Asp Cys Ala Asp Gly Ser Asp Glu Asn Ile Cys Thr Pro Asp
145                 150                 155                 160

Lys Asp Pro Asn Arg Ala Asp Val Cys Glu Pro Arg Thr Cys Leu Trp
                165                 170                 175

Ser Gln Gly Cys Phe Cys Ser Val Asp Gly Thr Arg Ile Pro Gly Asp
            180                 185                 190

Leu Thr Val Asp Gln Thr Pro Gln Met Ile Thr Ile Thr Phe Thr Gly
        195                 200                 205

Ala Ile Asn Glu Arg Asn Phe Arg Ile Phe Gln Asp Val Phe Lys Asp
    210                 215                 220

Thr Val Lys His Lys Gly Asn Asp Cys Thr Pro Lys Gly Thr Phe Phe
225                 230                 235                 240

Ile Ser His Gly Phe Ser Asn Tyr Ser Ala Ile Gln Glu Leu Asn Arg
                245                 250                 255

Val Gly His Glu Ile Ala Val Ser Ser Ile Thr Asn Asn Asp Asn Pro
```

```
                260                 265                 270
Asp Tyr Trp Ser Lys Leu Ser Ala Leu Asp Tyr Glu Ala Glu Met Asp
            275                 280                 285

Gly Ala Arg Leu Ile Ile Glu Lys Phe Ala Asn Ile Thr Ala Asn Glu
            290                 295                 300

Val Leu Gly Ile Arg Val Pro Lys Gln Arg Val Gly Gly Asn Arg Gln
305                 310                 315                 320

Phe Arg Met Met Val Asp Trp Gly Phe Leu Tyr Asp Ser Ser Ile Ser
                325                 330                 335

Ala Pro Met Gly Arg Leu Pro Leu Trp Pro Tyr Thr Leu Met His Arg
            340                 345                 350

Met Pro His Lys Cys Leu Gly Asn Asp Gln Asn Cys Pro Ser Gln Asn
            355                 360                 365

Phe Thr Val Trp Glu Met Val Ile Asn Glu Met Asp Arg Arg Asp Asp
            370                 375                 380

Pro Gln Phe Asp Glu Arg Leu Thr Gly Cys His Phe Val Asp Gln Cys
385                 390                 395                 400

Ala Asn Ile Gln Ser Pro Glu Gln Phe Arg Ala Phe Leu Asp Asn Asn
            405                 410                 415

Leu Ala Arg His Tyr Arg Thr Asn Arg Ala Pro Leu Gly Leu His Phe
            420                 425                 430

Thr Ser Gly Tyr Phe Glu Thr Arg Arg Asp Phe Leu Arg Glu Phe Val
            435                 440                 445

Lys Trp Val Arg Glu Thr Ala Leu Ser Gly Asp Tyr Phe Phe Val Thr
            450                 455                 460

Met Gln Gln Val Ile Asn Trp Met Glu Ala Pro Thr Glu Leu Thr Ala
465                 470                 475                 480

Ile Asn Asn Phe Gln Glu Trp Lys Gly Lys Cys Glu Val Lys Gly Gln
                485                 490                 495

Pro Tyr Cys Ser Leu Pro Asn Pro Cys Pro Lys Lys Val Pro Arg Ile
            500                 505                 510

Phe Pro Asn Glu Glu Met Phe Leu Tyr Thr Cys Met Glu Cys Pro
            515                 520                 525

Asn Thr Tyr Pro Trp Leu Gly Asp Pro His Gly Asn Gly Phe Leu Asp
            530                 535                 540

Ile Pro Asp Phe
545

<210> SEQ ID NO 2
<211> LENGTH: 11
<212> TYPE: PRT
<213> ORGANISM: Cherax quadricarinatus

<400> SEQUENCE: 2

Leu Phe Gln Asp Val Phe Lys Asp Ala Glu Lys
1               5                   10

<210> SEQ ID NO 3
<211> LENGTH: 13
<212> TYPE: PRT
<213> ORGANISM: Cherax quadricarinatus

<400> SEQUENCE: 3

Leu Ser Ala Leu Asp Tyr Glu Ala Glu Met Asp Gln Arg
1               5                   10
```

```
<210> SEQ ID NO 4
<211> LENGTH: 15
<212> TYPE: PRT
<213> ORGANISM: Cherax quadricarinatus

<400> SEQUENCE: 4

Ala Pro Leu Gly Leu His Phe Thr Ser Gly Tyr Phe Glu Thr Arg
1               5                   10                  15

<210> SEQ ID NO 5
<211> LENGTH: 19
<212> TYPE: PRT
<213> ORGANISM: Cherax quadricarinatus

<400> SEQUENCE: 5

Met Met Val Asp Trp Gly Phe Leu Tyr Asp Ser Ser Leu Ser Ala Pro
1               5                   10                  15

Met Gly Arg

<210> SEQ ID NO 6
<211> LENGTH: 11
<212> TYPE: PRT
<213> ORGANISM: Cherax quadricarinatus

<400> SEQUENCE: 6

His Gly Val Glu Leu Ala Val Ser Ser Leu Thr
1               5                   10

<210> SEQ ID NO 7
<211> LENGTH: 16
<212> TYPE: PRT
<213> ORGANISM: Cherax quadricarinatus

<400> SEQUENCE: 7

His Met Val Asp Gln Cys Ala Asn Leu Lys Ser Pro Glu Lys Phe Arg
1               5                   10                  15

<210> SEQ ID NO 8
<211> LENGTH: 13
<212> TYPE: PRT
<213> ORGANISM: Cherax quadricarinatus

<400> SEQUENCE: 8

Glu Leu Phe Phe Asp Val Gln Gln Gln Leu Cys Glu Arg
1               5                   10

<210> SEQ ID NO 9
<211> LENGTH: 285
<212> TYPE: PRT
<213> ORGANISM: Cherax quadricarinatus

<400> SEQUENCE: 9

Met Thr Thr Ile Met Leu Val Ile Leu Leu Val Gly Ala Cys Val Ala
1               5                   10                  15

Ile Pro Pro Gly Arg Pro Thr Asp Ser Ile Arg Phe Val Arg Gln Thr
                20                  25                  30

Lys Pro Leu Pro Arg Pro Gln His Pro Gln Ile Ser Pro Thr Pro Pro
            35                  40                  45

Ala Gly Tyr Gln Pro Lys Pro Gln Val Asp Pro Thr Pro His Pro Gly
        50                  55                  60

His Val Ile Gln Thr Leu Pro Ala His Pro Ser Ser Lys Leu Thr Arg
65                  70                  75                  80
```

```
Pro Ala Pro Arg Pro Ser Arg His Gln Arg Ser Ala Asp Glu Val Arg
                85                  90                  95

Gln Gly Ser Val Pro Thr Thr Ala Ile Gly Lys Pro Gln Thr Leu Pro
            100                 105                 110

Pro Lys Ser Gln Leu Thr Lys Pro Ala Val Arg Pro Gln Thr Arg Pro
        115                 120                 125

Ala Thr Leu Pro Gly Asn Leu Ala Lys Pro Ala Gln Arg Ser Lys Ser
    130                 135                 140

Leu Glu Asp Ser Ser Phe Ala Pro Leu Pro Thr Gly Pro Ile Val Glu
145                 150                 155                 160

Pro Arg Pro Ser Pro Gly Glu Leu Thr Lys Pro Ala Ser Arg Pro Ile
                165                 170                 175

Val Asp Pro Ile Pro Ala Gly Glu Leu Thr Lys Pro Ala Ser Arg
                180                 185                 190

Pro Ile Val Asp Pro Ile Pro Ala Gly Glu Leu Thr Lys Pro Ala
        195                 200                 205

Ser Arg Pro Ile Val Asp Pro Ile Pro Ala Gly Glu Leu Thr Lys
    210                 215                 220

Pro Ala Asn Arg Pro Lys Ser Val Asp Ser Gly Phe Ala Pro Leu Pro
225                 230                 235                 240

Thr Gly Pro Ile Val Glu Pro Arg Pro Pro Gly Glu Leu Thr Lys
                245                 250                 255

Pro Ala Pro Arg Pro Arg Pro Arg Pro Gly Asp Leu Thr Lys Pro Ala
                260                 265                 270

Thr Arg Pro Arg Pro Arg Pro Ala Arg Pro Thr Gln Ala
        275                 280                 285

<210> SEQ ID NO 10
<211> LENGTH: 9
<212> TYPE: PRT
<213> ORGANISM: Cherax quadricarinatus

<400> SEQUENCE: 10

Pro Ala Thr Leu Pro Phe His Ala Lys
1               5

<210> SEQ ID NO 11
<211> LENGTH: 6
<212> TYPE: PRT
<213> ORGANISM: Cherax quadricarinatus

<400> SEQUENCE: 11

Ser Gln Leu Thr Lys Pro
1               5

<210> SEQ ID NO 12
<211> LENGTH: 5
<212> TYPE: PRT
<213> ORGANISM: Cherax quadricarinatus

<400> SEQUENCE: 12

Glu Leu Pro Pro Lys
1               5

<210> SEQ ID NO 13
<211> LENGTH: 17
<212> TYPE: PRT
<213> ORGANISM: Cherax quadricarinatus

<400> SEQUENCE: 13
```

```
Gln Gly Ser Val Pro Thr Thr Gln Leu Gln Val Lys Pro Asp Pro Pro
1               5                   10                  15

Lys

<210> SEQ ID NO 14
<211> LENGTH: 16
<212> TYPE: PRT
<213> ORGANISM: Cherax quadricarinatus

<400> SEQUENCE: 14

Pro Leu Val Asp Pro Leu His Gly Asn Cys Pro Cys Cys Asn Tyr Arg
1               5                   10                  15

<210> SEQ ID NO 15
<211> LENGTH: 19
<212> TYPE: PRT
<213> ORGANISM: Cherax quadricarinatus

<400> SEQUENCE: 15

Trp Asp Ser Gly Phe Ala Pro Leu Pro Thr Gly Pro Leu Val Glu Arg
1               5                   10                  15

Pro Arg Val

<210> SEQ ID NO 16
<211> LENGTH: 15
<212> TYPE: PRT
<213> ORGANISM: Cherax quadricarinatus

<400> SEQUENCE: 16

Glu Asp Ser Ser Phe Ala Gln Leu Trp Phe Thr Val Glu Pro Arg
1               5                   10                  15

<210> SEQ ID NO 17
<211> LENGTH: 202
<212> TYPE: PRT
<213> ORGANISM: Cherax quadricarinatus

<400> SEQUENCE: 17

Met Arg Ala Val Val Cys Val Leu Leu Ala Ile Ser Gly Met Ala Ser
1               5                   10                  15

Ala Gln Ser Ala Arg Gly Glu Thr Phe Ala His Ala Arg Pro Ser Val
                20                  25                  30

Asn Ser Phe Gln Asp Ser Ala Ser Leu Ser Asp Pro Ser Ala Ala
            35                  40                  45

Ala Ala Pro Arg Ala Ala Pro Ala Ala Ala Pro Ala Ala Pro Ala
        50                  55                  60

Ala Ala Pro Ala Gln Gln Asn Tyr Gly Pro Asn Phe Phe Gly Pro Gly
65                  70                  75                  80

Leu Asn Asn Pro Leu Ala Phe Pro Leu Asn Pro Leu Val Ala Gln Gln
                85                  90                  95

Ala Gln Arg Ile Ala Ser Phe Asn Pro Asn Leu Arg Val Phe Val Asp
            100                 105                 110

Ile Asp Gly Ser Val Gln Leu Thr Asp Gln Phe Gly Arg Glu Val Asp
        115                 120                 125

Glu Val Leu Asp Glu Phe Gly Arg Asp Val Ser Glu Leu Leu Asp Val
    130                 135                 140

Glu Glu Gln Gln Glu Ala Leu Leu Arg Arg Arg Gln Gln Gln Leu Asp
145                 150                 155                 160
```

```
Leu Gln Leu Leu Gln Gln Phe Asn Asn Pro Ala Phe Gly Gly Ser Val
            165                 170                 175

Gly Gly Gln Ala Ala Val Gly Gly Gln Thr Gly Val Gly Gly Gly Phe
        180                 185                 190

Pro Arg Gln Arg Ser Phe Arg Ile Val Val
        195                 200

<210> SEQ ID NO 18
<211> LENGTH: 11
<212> TYPE: PRT
<213> ORGANISM: Cherax quadricarinatus

<400> SEQUENCE: 18

Glu Val Glu Glu Leu Leu Asp Glu Phe Gly Arg
1               5                   10

<210> SEQ ID NO 19
<211> LENGTH: 12
<212> TYPE: PRT
<213> ORGANISM: Cherax quadricarinatus

<400> SEQUENCE: 19

Ser Thr Ala Ala Ala Pro Ala Ala Ala Ala Ala Arg
1               5                   10

<210> SEQ ID NO 20
<211> LENGTH: 12
<212> TYPE: PRT
<213> ORGANISM: Cherax quadricarinatus

<400> SEQUENCE: 20

Pro Leu Asn Pro Leu Val Ala Gln Gln Ala Gln Arg
1               5                   10

<210> SEQ ID NO 21
<211> LENGTH: 17
<212> TYPE: PRT
<213> ORGANISM: Cherax quadricarinatus

<400> SEQUENCE: 21

Val Phe Val Asp Val Asp Gly Ser Ala His Phe Thr Asp Gln Phe Gly
1               5                   10                  15

Arg

<210> SEQ ID NO 22
<211> LENGTH: 17
<212> TYPE: PRT
<213> ORGANISM: Cherax quadricarinatus

<400> SEQUENCE: 22

Asp Val Ser Glu Leu Leu Asp Val Gln Glu Gln Gln Glu Gln Leu Ala
1               5                   10                  15

Arg

<210> SEQ ID NO 23
<211> LENGTH: 10
<212> TYPE: PRT
<213> ORGANISM: Cherax quadricarinatus

<400> SEQUENCE: 23

Cys Asn Leu Asn Asn Pro Leu Ala Leu Val
1               5                   10
```

<210> SEQ ID NO 24
<211> LENGTH: 113
<212> TYPE: PRT
<213> ORGANISM: Cherax quadricarinatus

<400> SEQUENCE: 24

```
Met Lys Ile Phe Ile Leu Leu Val Val Ile Gly Val Val Ser Ala Gln
 1               5                  10                  15
Leu Gly Ala Gly Gln Val Gly Gly Ala Ala Pro Ala Gln Gly Ala Gly
            20                  25                  30
Gly Ala Ala Gly Val Gly Gly Pro Gly Ala Ala Pro Val Asn Pro Tyr
        35                  40                  45
Gly Pro Lys Val Tyr Gly Ser Gly Leu Asn Asn Pro Phe Ala Phe Pro
    50                  55                  60
His Asn Thr Trp Glu Val Ser Arg Ala Ala Val Ala Ala Thr Asn
 65                 70                  75                  80
Pro Asn Leu Tyr Val Arg Val Glu Ser Asp Gly Gly Trp Glu Phe Thr
                85                  90                  95
Asn Arg Phe Gly Glu Lys Val Asp Val Tyr Asn Ser Phe Gly Gln Glu
            100                 105                 110
Leu
```

<210> SEQ ID NO 25
<211> LENGTH: 12
<212> TYPE: PRT
<213> ORGANISM: Cherax quadricarinatus

<400> SEQUENCE: 25

```
Val Glu Ser Asp Gly Gly Trp Glu Phe Thr Asn Arg
 1               5                  10
```

<210> SEQ ID NO 26
<211> LENGTH: 14
<212> TYPE: PRT
<213> ORGANISM: Cherax quadricarinatus

<400> SEQUENCE: 26

```
Ala Ala Ala Val Ala Ala Thr Asn Pro Leu Asn Tyr Val Arg
 1               5                  10
```

<210> SEQ ID NO 27
<211> LENGTH: 21
<212> TYPE: PRT
<213> ORGANISM: Cherax quadricarinatus

<400> SEQUENCE: 27

```
Val Tyr Gly Ser Gly Leu Asn Asn Pro Phe Ala Phe Pro His Ser Gln
 1               5                  10                  15
Trp Glu Val Ser Arg
            20
```

<210> SEQ ID NO 28
<211> LENGTH: 12
<212> TYPE: PRT
<213> ORGANISM: Cherax quadricarinatus

<400> SEQUENCE: 28

```
Ala Gly Val Gly Gly Lys Pro Ala His Pro Val Lys
 1               5                  10
```